US012629470B2

(12) United States Patent
Le Gal Redon et al.

(10) Patent No.: US 12,629,470 B2
(45) Date of Patent: **\*May 19, 2026**

(54) DRUG DELIVERY DEVICE WITH NEEDLE HUB

(71) Applicant: Becton, Dickinson and Company, Franklin Lakes, NJ (US)

(72) Inventors: Patrick Le Gal Redon, Seyssinet-Pariset (FR); Steve Beguin, Rathdrum (IE); Marko Plevnik, London (GB); Nathan Lyell, Woking (GB); Etienne Jean-Baptiste Louis Chenel, Warwick (GB); William Geoffrey Arthur Marsh, Stratford-upon-Avon (GB); Malcolm Stanley Boyd, Wellesbourne (GB); Zoe Georgina Armstrong, Leamington Spa (GB)

(73) Assignee: Becton, Dickinson and Company, Franklin Lakes, NJ (US)

( \* ) Notice: Subject to any disclaimer, the term of this patent is extended or adjusted under 35 U.S.C. 154(b) by 573 days.

This patent is subject to a terminal disclaimer.

(21) Appl. No.: 17/569,223

(22) Filed: Jan. 5, 2022

(65) Prior Publication Data

US 2022/0211940 A1 Jul. 7, 2022

Related U.S. Application Data

(60) Provisional application No. 63/134,054, filed on Jan. 5, 2021.

(51) Int. Cl.
| | |
|---|---|
| *A61M 5/142* | (2006.01) |
| *A61M 5/158* | (2006.01) |
| *A61M 5/162* | (2006.01) |

(52) U.S. Cl.
CPC .... *A61M 5/14248* (2013.01); *A61M 5/14244* (2013.01); *A61M 5/158* (2013.01);
(Continued)

(58) Field of Classification Search
CPC .......... A61M 5/14244; A61M 5/14248; A61M 2005/14252; A61M 2005/14256;
(Continued)

(56) References Cited

U.S. PATENT DOCUMENTS

| | | | |
|---|---|---|---|
| 4,284,077 A | 8/1981 | Wagner | |
| 5,267,963 A | 12/1993 | Bachynsky | |

(Continued)

FOREIGN PATENT DOCUMENTS

| | | |
|---|---|---|
| JP | 2002528234 A | 9/2002 |
| JP | 2006501043 A | 1/2006 |

(Continued)

*Primary Examiner* — Kami A Bosworth
*Assistant Examiner* — Avery Smale
(74) *Attorney, Agent, or Firm* — The Webb Law Firm

(57) ABSTRACT

A drug delivery device includes a housing, a fluid reservoir received within the housing, a drive assembly configured to dispense fluid from the fluid reservoir, a needle hub actuator attached to the housing, and a needle hub at least partially received by the housing. The needle hub includes a hub body, a needle holder with a needle attached to the needle holder, and a cannula holder with a cannula attached to the cannula holder. The needle hub actuator is configured to move the needle holder and the cannula holder from a retracted position where the needle and the cannula are positioned within the hub body to an insertion position where the needle and the cannula are positioned within the hub body. The needle hub is detachable from the housing.

14 Claims, 41 Drawing Sheets

(52) U.S. Cl.
CPC ... *A61M 5/162* (2013.01); *A61M 2005/14252* (2013.01); *A61M 2005/14256* (2013.01); *A61M 2005/1426* (2013.01); *A61M 2005/1585* (2013.01); *A61M 2005/1586* (2013.01); *A61M 2005/1587* (2013.01)

(58) Field of Classification Search
CPC .. A61M 2005/1426; A61M 2005/1585; A61M 2005/1587; A61M 5/158; A61M 5/162; A61M 2005/1586

See application file for complete search history.

(56) References Cited

U.S. PATENT DOCUMENTS

| | | | |
|---|---|---|---|
| 6,607,543 B2 | 8/2003 | Purcell et al. | |
| 7,250,037 B2 | 7/2007 | Shermer et al. | |
| 7,931,621 B2 | 4/2011 | Cross et al. | |
| 8,795,234 B2 | 8/2014 | Kadamus et al. | |
| 9,466,757 B2 | 10/2016 | Modi et al. | |
| 9,504,785 B2 | 11/2016 | Forsell | |
| 9,533,092 B2 | 1/2017 | Gyrn | |
| 10,434,247 B2* | 10/2019 | Cole | A61M 5/14248 |
| 10,434,285 B2 | 10/2019 | Schoonmaker et al. | |
| 10,933,191 B2 | 3/2021 | Lawrence et al. | |
| 11,103,636 B2 | 8/2021 | Olivas et al. | |
| 2002/0123740 A1 | 9/2002 | Flaherty et al. | |
| 2004/0158207 A1 | 8/2004 | Hunn et al. | |
| 2005/0273019 A1 | 12/2005 | Conway et al. | |
| 2006/0161108 A1 | 7/2006 | Mogensen et al. | |
| 2008/0051738 A1* | 2/2008 | Griffin | A61M 5/158 604/272 |
| 2008/0058719 A1 | 3/2008 | Edwards et al. | |
| 2008/0195049 A1 | 8/2008 | Thalmann et al. | |
| 2008/0215006 A1 | 9/2008 | Thorkild | |
| 2009/0012472 A1 | 1/2009 | Ahm et al. | |
| 2009/0054866 A1 | 2/2009 | Teisen-Simony et al. | |
| 2010/0049129 A1 | 2/2010 | Yokoi et al. | |
| 2010/0100048 A1 | 4/2010 | Nielsen et al. | |
| 2011/0270220 A1 | 11/2011 | Genosar | |
| 2011/0270232 A1 | 11/2011 | Forsell | |
| 2011/0275996 A1 | 11/2011 | Gyory et al. | |
| 2012/0143135 A1* | 6/2012 | Cole | A61M 5/158 604/164.12 |

| | | | |
|---|---|---|---|
| 2013/0012889 A1 | 1/2013 | Schraga | |
| 2013/0060233 A1 | 3/2013 | O'Connor et al. | |
| 2014/0058353 A1 | 2/2014 | Politis et al. | |
| 2014/0088509 A1* | 3/2014 | Sonderegger | A61M 5/3287 604/157 |
| 2014/0316379 A1 | 10/2014 | Sonderegger et al. | |
| 2015/0005716 A1 | 1/2015 | Adair et al. | |
| 2016/0058941 A1 | 3/2016 | Wu et al. | |
| 2016/0296695 A1 | 10/2016 | Hassman et al. | |
| 2017/0021137 A1 | 1/2017 | Cole | |
| 2017/0043133 A1 | 2/2017 | Amano et al. | |
| 2017/0259011 A1 | 9/2017 | Nielsen | |
| 2018/0021508 A1* | 1/2018 | Destefano | A61M 5/14244 604/151 |
| 2019/0015584 A1 | 1/2019 | Meehan et al. | |
| 2019/0053465 A1 | 2/2019 | Knight et al. | |
| 2019/0060562 A1 | 2/2019 | Olivas et al. | |
| 2019/0175840 A1 | 6/2019 | Schabbach et al. | |
| 2019/0336679 A1 | 11/2019 | Staub et al. | |
| 2019/0365986 A1 | 12/2019 | Coiner et al. | |
| 2019/0365993 A1* | 12/2019 | Staub | A61M 5/3287 |
| 2019/0388615 A1 | 12/2019 | Sonderegger et al. | |
| 2020/0001005 A1 | 1/2020 | Politis et al. | |
| 2020/0164155 A1 | 5/2020 | Mojarrad et al. | |
| 2020/0238004 A1 | 7/2020 | McCullough | |
| 2020/0360235 A1 | 11/2020 | Moller | |

FOREIGN PATENT DOCUMENTS

| | | |
|---|---|---|
| JP | 2008528086 A | 7/2008 |
| JP | 2012115674 A | 6/2012 |
| JP | 2014510573 A | 5/2014 |
| JP | 201655205 A | 4/2016 |
| JP | 2017513622 A | 6/2017 |
| JP | 2018505031 A | 2/2018 |
| JP | 2020505175 A | 2/2020 |
| JP | 2020508117 A | 3/2020 |
| WO | 0025844 A1 | 5/2000 |
| WO | 2004032990 A2 | 4/2004 |
| WO | 2006077262 A1 | 7/2006 |
| WO | 2012134589 A1 | 10/2012 |
| WO | 2015164653 A1 | 10/2015 |
| WO | 2016130679 A2 | 8/2016 |
| WO | 2018152073 A1 | 8/2018 |

* cited by examiner

1. REMOVE PACKAGING    2. REMOVE ADHESIVE    3. ATTACH TO SKIN

4. SQUEEZE BUTTON TO       5. NEEDLE AUTOMATICALLY    6. INFUSE
   INSERT NEEDLE              RETRACTS LEAVING AN
                              INDWELLING CATHETER

7. INFUSION COMPLETE       8. PULL TAB               9. REMOVE DEVICE
                             (CATHETER RETRACTS)

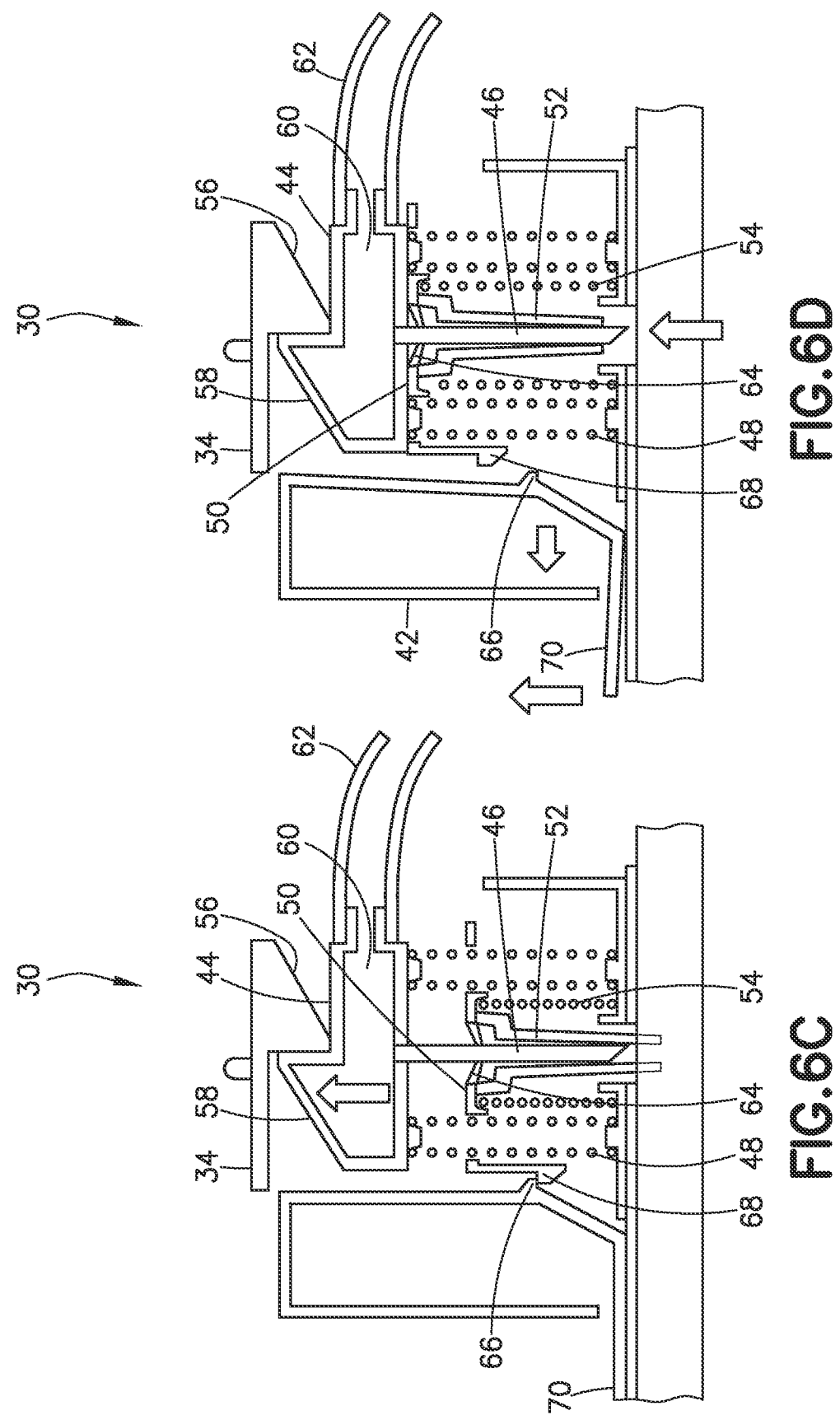

152

1. REMOVE PACKAGING     2. REMOVE ADHESIVE     3. ATTACH TO SKIN     4. SYRINGE PUMP IS ACTEVATED AND NEEDLE INSERTS

5. NEEDLE AUTOMATICALLY RETRACTS LEAVING AN IN-DWELLING CATHETER     6. INFUSE     7. INFUSION COMPLETE

184

9. REMOVE DEVICE (CATHETER AUTOMATICALLY RETRACTS)

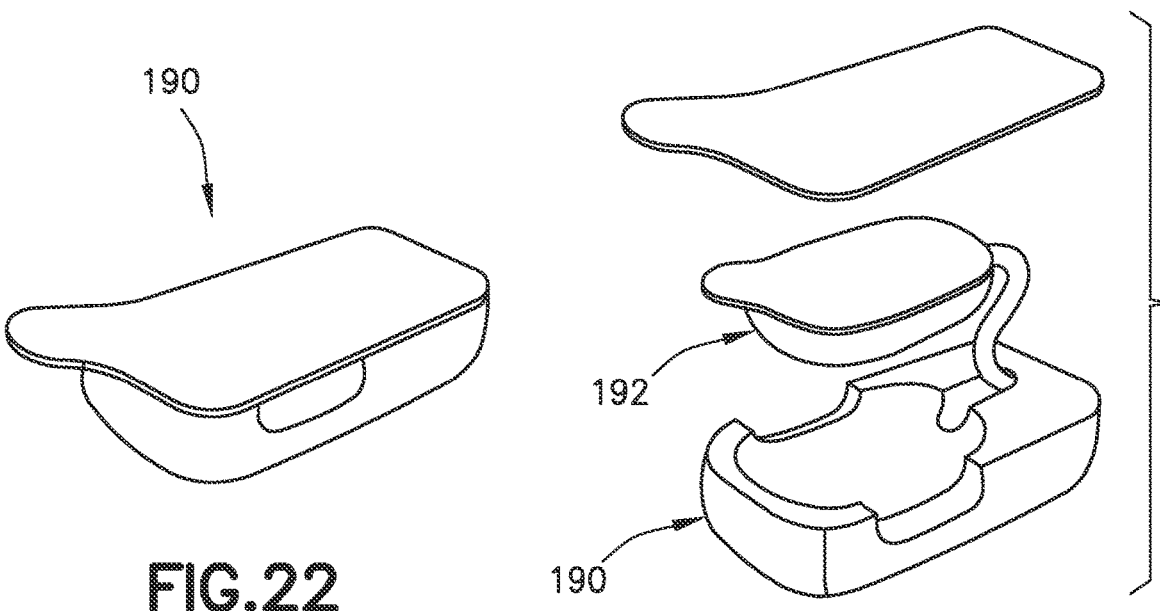
FIG.22
FIG.23
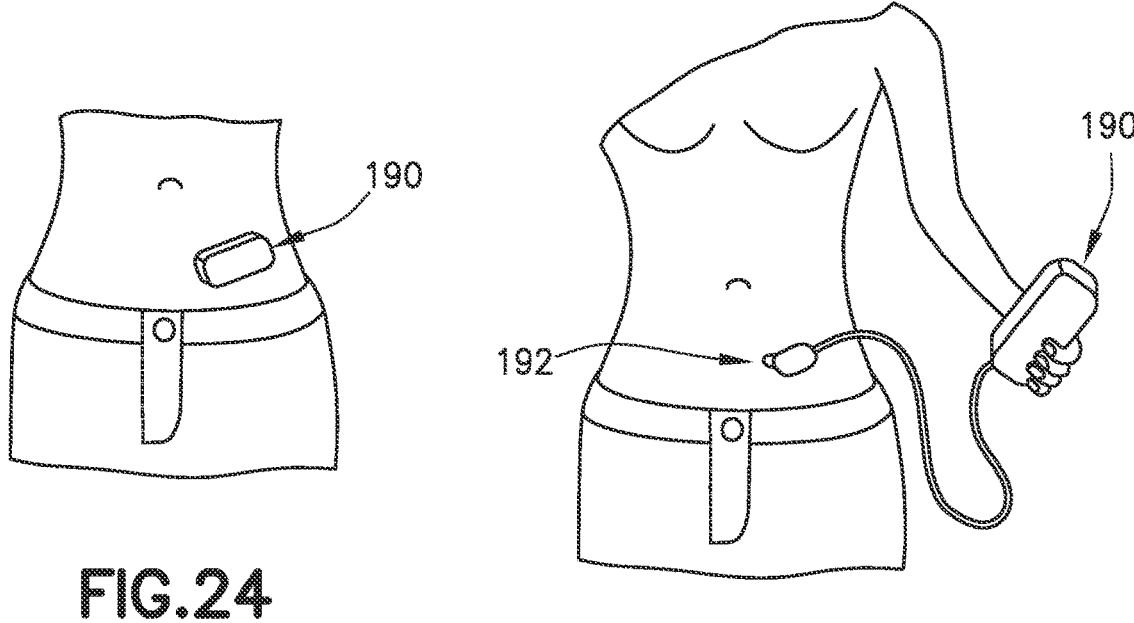
FIG.24
FIG.25

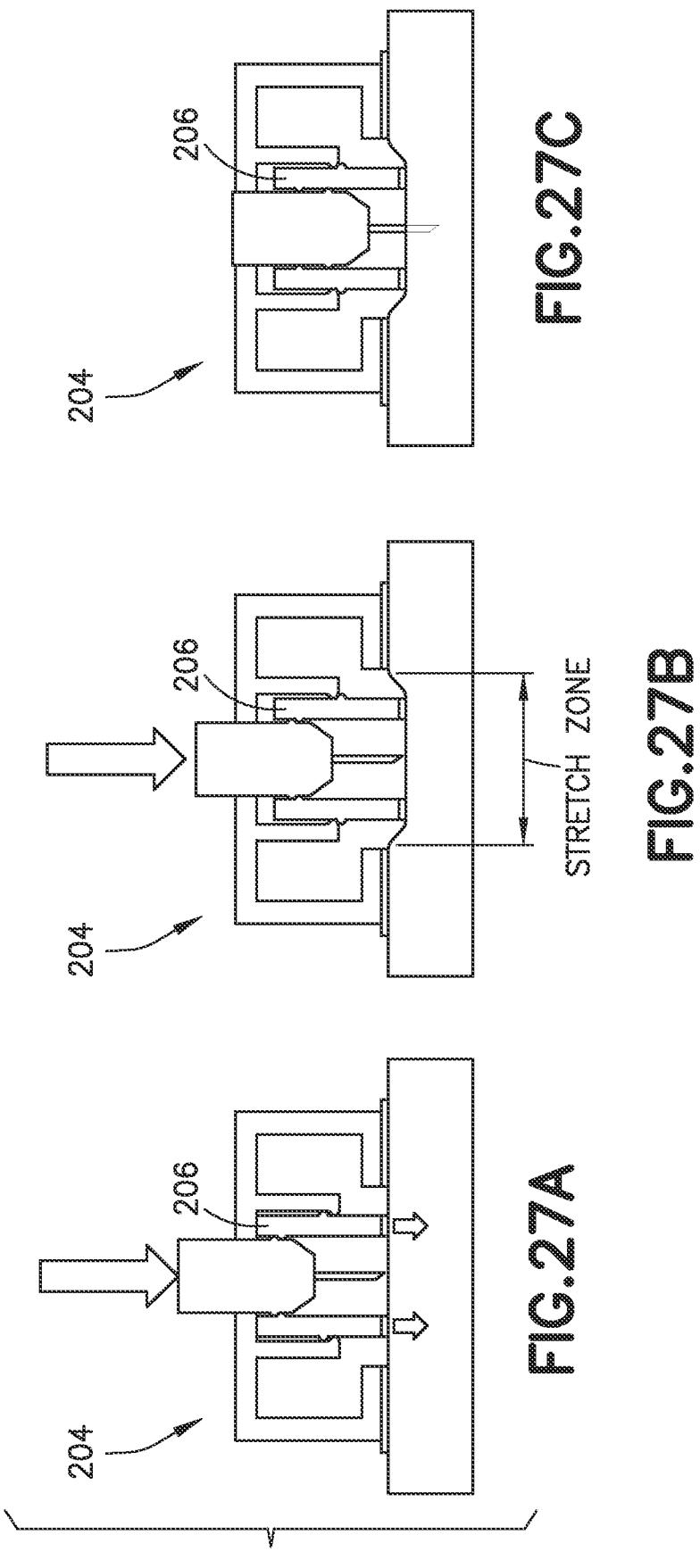

DRUG DELIVERY DEVICE WITH NEEDLE HUB

CROSS-REFERENCE TO RELATED APPLICATION

This application claims priority to U.S. Provisional Application No. 63/134,054, filed Jan. 5, 2021, which is hereby incorporated by reference in its entirety.

BACKGROUND OF THE INVENTION

Field of the Invention

The present disclosure relates to a drug delivery device with a needle hub.

Description of Related Art

Wearable medical devices, such as automatic injectors, have the benefit of providing therapy to the patient at a location remote from a clinical facility and/or while being worn discretely under the patient's clothing. The wearable medical device can be applied to the patient's skin and configured to automatically deliver a dose of a pharmaceutical composition within a predetermined time period after applying the wearable medical device to the patient's skin. After the device delivers the pharmaceutical composition to the patient, the patient may subsequently remove and dispose of the device.

SUMMARY OF THE INVENTION

In one aspect or embodiment, a drug delivery device includes a housing, a fluid reservoir received within the housing, a drive assembly configured to dispense fluid from the fluid reservoir, a needle hub actuator attached to the housing, and a needle hub at least partially received by the housing. The needle hub includes a hub body having a patient contact surface and a housing connection attaching the hub body to the housing, a needle holder with a needle attached to the needle holder, and a cannula holder with a cannula attached to the cannula holder. The needle hub actuator is configured to move the needle holder and the cannula holder from a retracted position where the needle and the cannula are positioned within the hub body to an insertion position where the needle and the cannula are positioned within the hub body. The needle hub is detachable from the housing.

The needle hub actuator may include a needle holder connector and the needle holder may include an actuator connector, with the needle holder connector configured to be connected to the actuator connector. The hub body may define a cam track and the needle holder may include a cam member received within the cam track, where axial displacement of the needle holder is configured to rotate the needle holder to connect the needle holder connector of the needle hub actuator to the actuator connector of the needle holder. The needle holder connector of the needle hub actuator and the actuator connector of the needle holder may form a bayonet connector.

The hub body may include a cannula lock configured to secure the cannula holder in the insertion position. The cannula lock may include a protrusion configured to engage the cannula holder when the cannula holder is in the insertion position. The hub body may include a needle protrusion configured to engage the needle holder when the needle holder is in the retracted position, and the hub body may include a cannula protrusion configured to engage the cannula holder when the cannula holder is in the retracted position.

The hub body may define a cannula track and the cannula holder may define a track protrusion received within the cannula track, where the cannula track is linear.

The housing connection of the hub body may be received within an opening defined by the housing. The housing connection may include a retaining member configured to engage the housing to secure the hub body to the housing. The housing connection may include a release member configured to be engaged by the needle hub actuator to release the hub body from the housing. The retaining member and the release member may be positioned on an extension, with the extension configured to be biased radially outward.

The patient contact surface may include an adhesive pad configured to secure the hub body to a skin surface of a person. The cannula holder may include a seal engaged with the needle. The cannula holder may include a port in fluid communication with the cannula, where the port of the cannula holder is in fluid communication with the fluid reservoir via tubing. The tubing may be received within a slot defined by the hub body. The needle holder and the cannula holder may be configured to be positioned within the housing when the needle hub actuator moves the needle holder and the cannula holder from the retracted position to the insertion position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

FIG. 6C is a schematic view of the needle hub of FIG. 3, showing a needle in a retracted position and a cannula in an insertion position.

FIG. 6D is a schematic view of the needle hub of FIG. 3, showing movement of a cannula to a retracted position.

FIG. 22 is a perspective view of a drug delivery device and a needle hub according to a further aspect or embodiment of the present application.

FIG. 23 is an exploded perspective view of the drug delivery device and the needle hub of FIG. 22.

FIG. 24 is a perspective view of the drug delivery device and the needle hub of FIG. 22, showing the drug delivery device and the needle hub connected while delivering a medicament.

FIG. 25 is a perspective view of the drug delivery device and the needle hub of FIG. 22, showing the needle hub separated from the drug delivery device while delivering a medicament.

FIG. 27A is a cross-sectional view of a needle hub according to a further aspect or embodiment of the present application, showing an initial position of the needle hub.

FIG. 27B is a cross-sectional view of a needle hub according to a further aspect or embodiment of the present application, showing engagement with a skin surface.

FIG. 27C is a cross-sectional view of a needle hub according to a further aspect or embodiment of the present application, showing insertion of a needle.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". By "about" is meant a range of plus or minus ten percent of the stated value. As used in the specification and the claims, the singular form of "a", "an", and "the" include plural referents unless the context clearly dictates otherwise. The terms "first", "second", and the like are not intended to refer to any particular order or chronology, but instead refer to different conditions, properties, or elements. By "at least" is meant "greater than or equal to".

Figure 1:
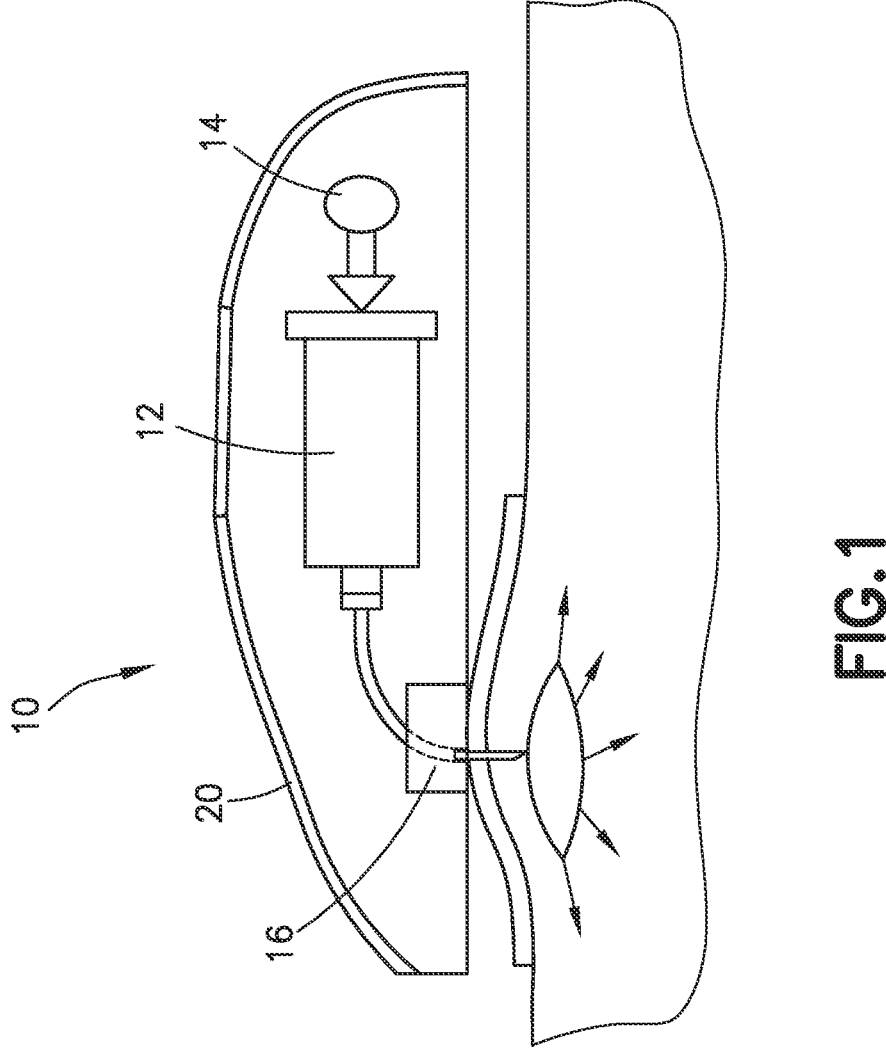
FIG. 1 is a schematic view of a drug delivery device according to one aspect or embodiment of the present application.
Figure 2:
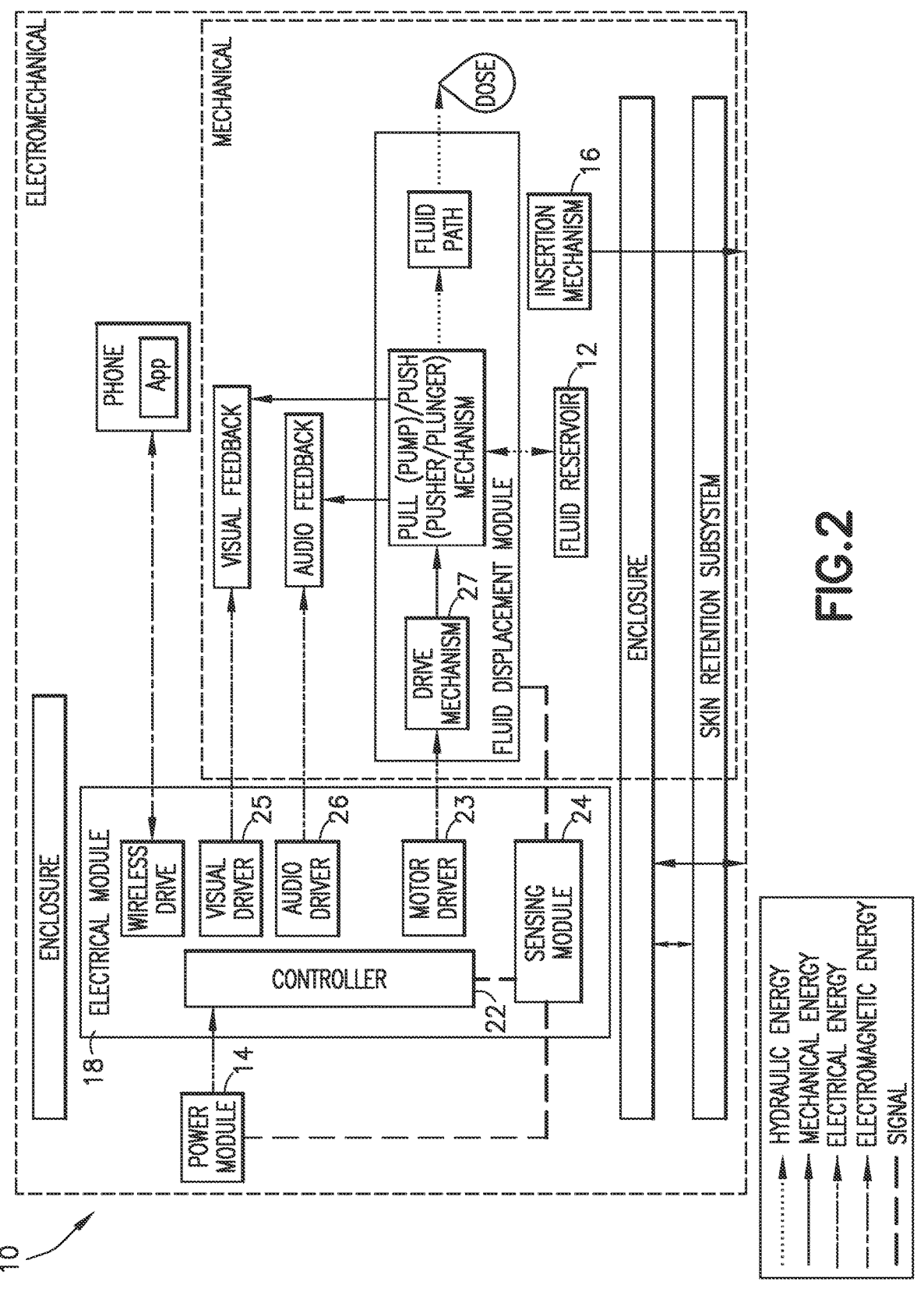
FIG. 2 is a schematic view of the drug delivery device of FIG. 1.
Figure 3:
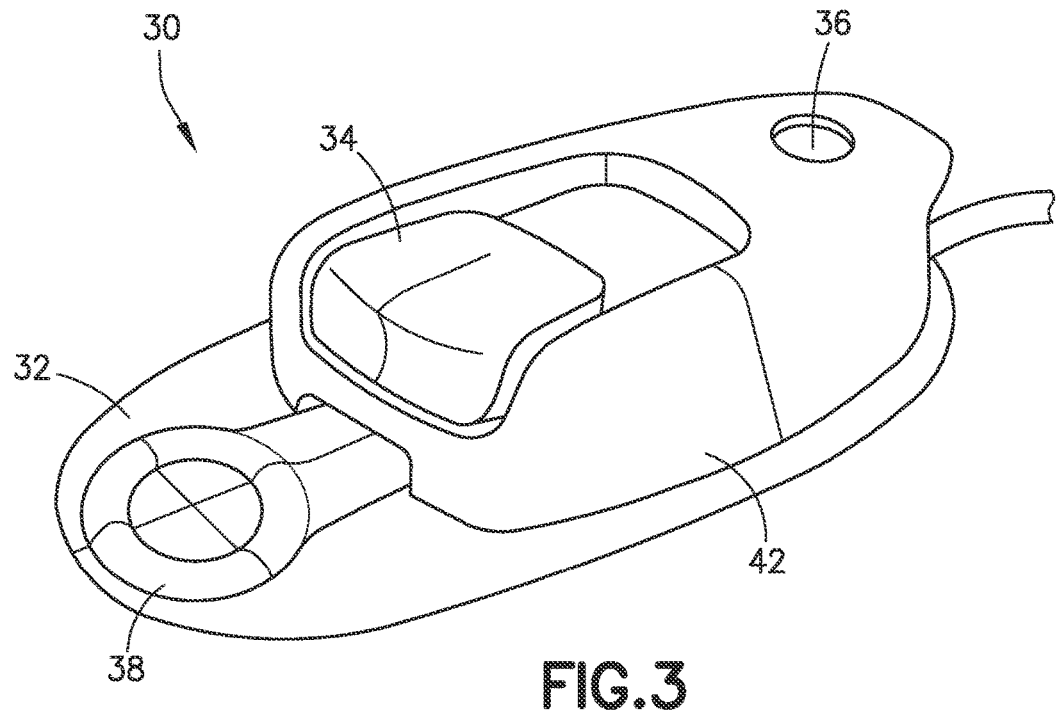
FIG. 3 is a perspective view of a needle hub according to one aspect or embodiment of the present application.
Figures 4A, 4B, 4C:
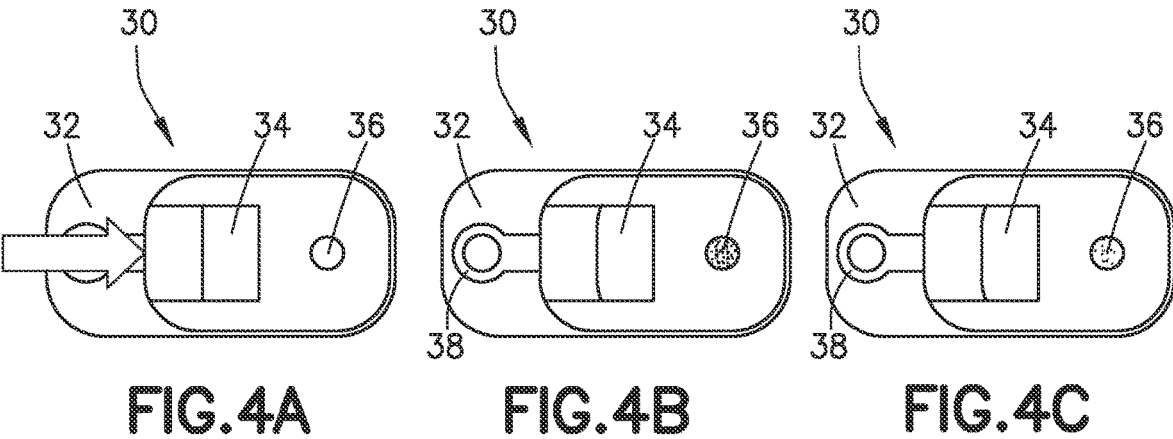
FIG. 4A is a top view of the needle hub of FIG. 3, showing an indicator prior to use of the needle hub.
FIG. 4B is a top view of the needle hub of FIG. 3, showing an indicator after insertion of a needle.
FIG. 4C is a top view of the needle hub of FIG. 3, showing an indicator after withdrawal of a cannula.

Referring to FIGS. 1-3, a drug delivery device 10 includes a reservoir 12, a power module 14, an insertion mechanism 16, control electronics 18, and a housing 20. In one aspect or embodiment, the drug delivery device 10 is a wearable automatic injector. The drug delivery device 10 may be mounted onto the skin of a patient and triggered to inject a pharmaceutical composition from the reservoir 12 into the patient. The drug delivery device 10 may be pre-filled with the pharmaceutical composition, or it may be filled with the pharmaceutical composition by the patient or medical professional prior to use. The control electronics 18 may include a processor 22, such as a microcontroller, a motor driver 23, a sensing module 24, a visual driver 25, and/or audio driver 26. The drug delivery device 10 includes a drive mechanism 27 configured to dispense fluid from the reservoir 12. The drive mechanism 27 may be motor powered, spring powered, hydraulic powered, pneumatic powered, and/or other suitable drive mechanism.

The drug delivery device 10 is configured to deliver a dose of a pharmaceutical composition, e.g., any desired medicament, into the patient's body by a subcutaneous injection at a slow, controlled injection rate. Exemplary time durations for the delivery achieved by the drug delivery device 10 may range from about 5 minutes to about 60 minutes, but are not limited to this exemplary range. Exemplary volumes of the pharmaceutical composition delivered by the drug delivery device 10 may range from about 10 milliliters to about 50 milliliters, but are not limited to this exemplary range. The volume of the pharmaceutical composition delivered to the patient may be adjusted. The device 10 may communicate with another device, such as a mobile device or computer.

Figure 5:
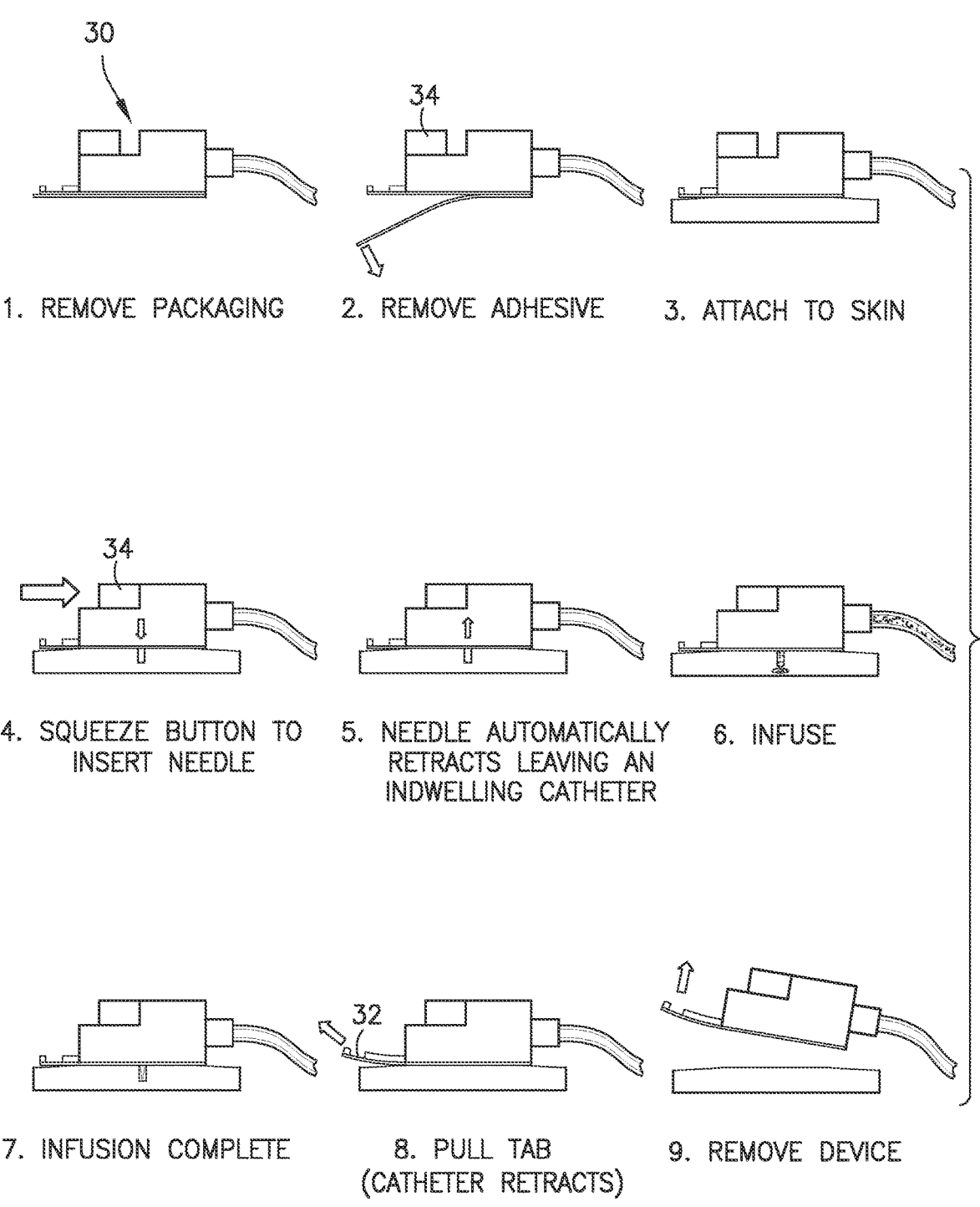
FIG. 5 is a schematic view showing a method of using the needle hub of FIG. 3.
Figures 6A, 6B:
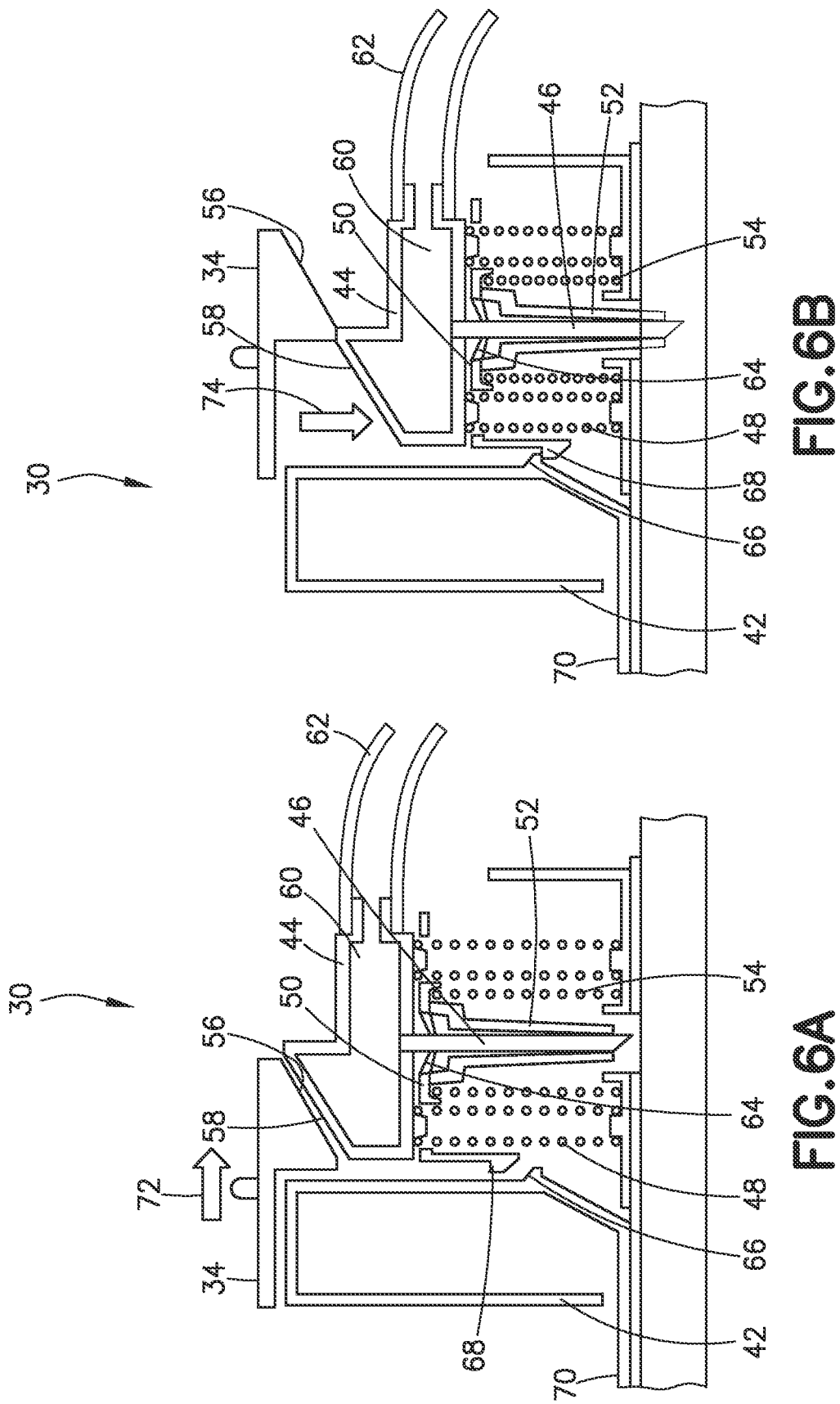
FIG. 6A is a schematic view of the needle hub of FIG. 3, showing actuation of an activation button.
FIG. 6B is a schematic view of the needle hub of FIG. 3, showing movement of a needle and cannula from a retracted position to an insertion position.
Figure 7:
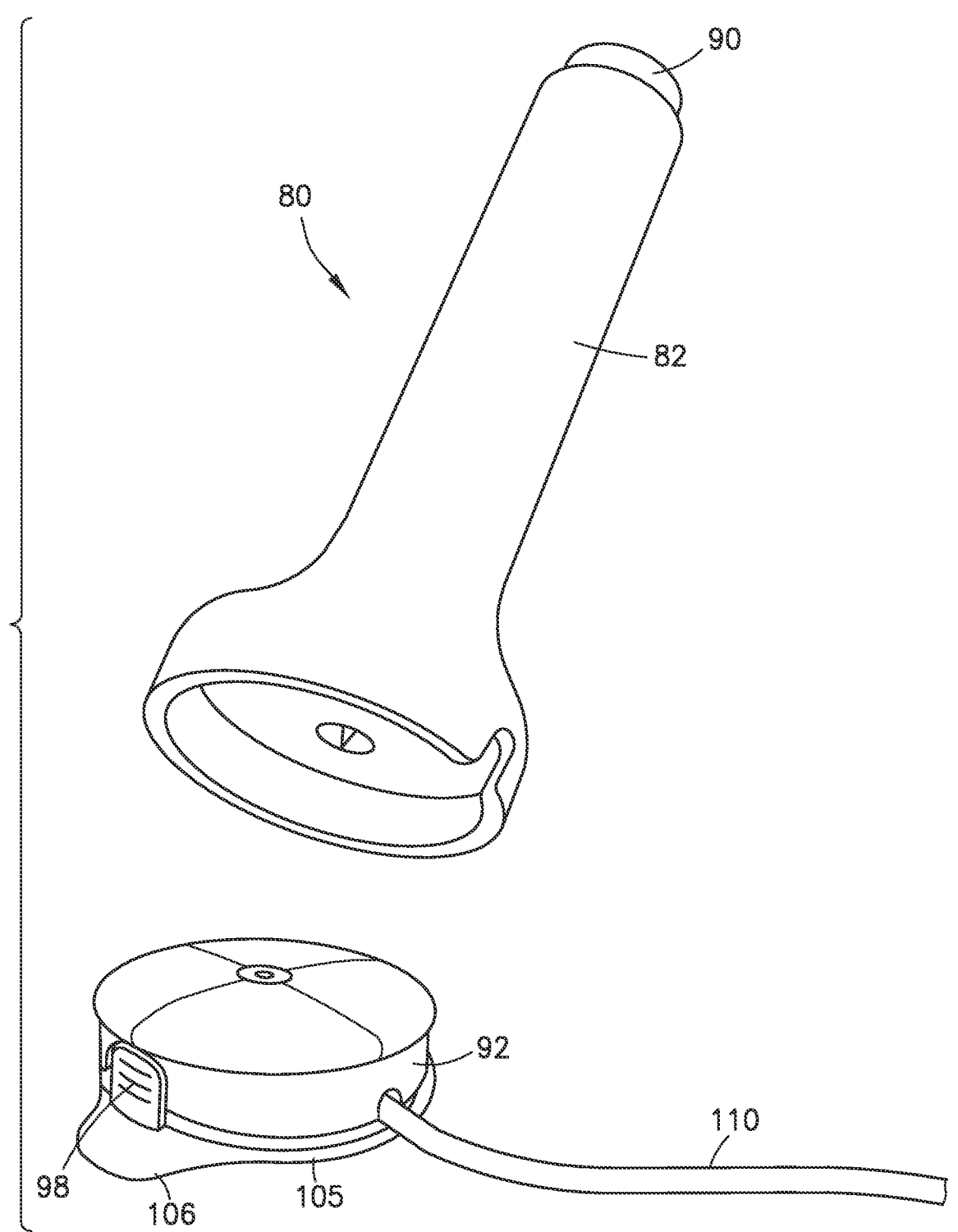
FIG. 7 is a perspective view of a needle hub according to a further aspect or embodiment of the present application.
Figure 8:
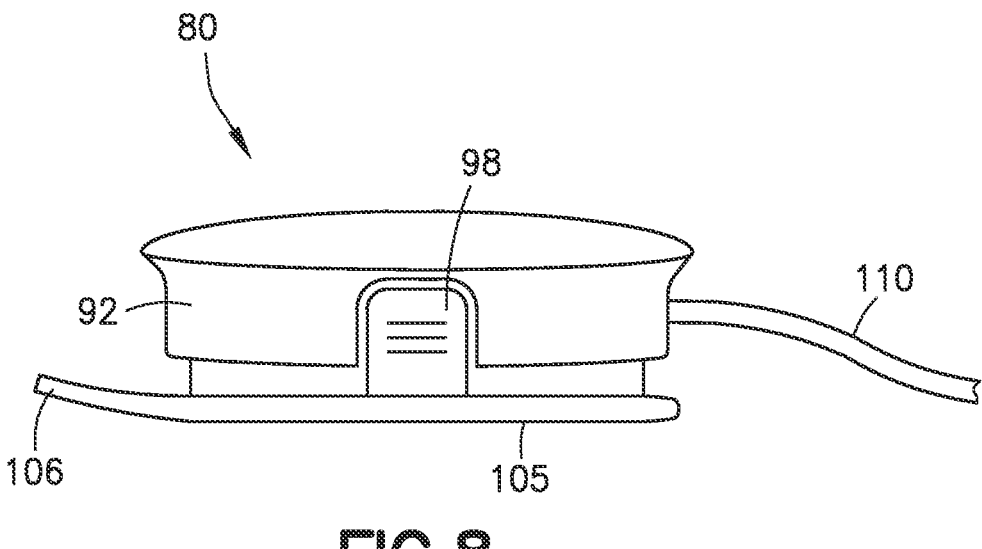
FIG. 8 is a front view of the needle hub of FIG. 7, showing an infusion mode.
Figure 9:
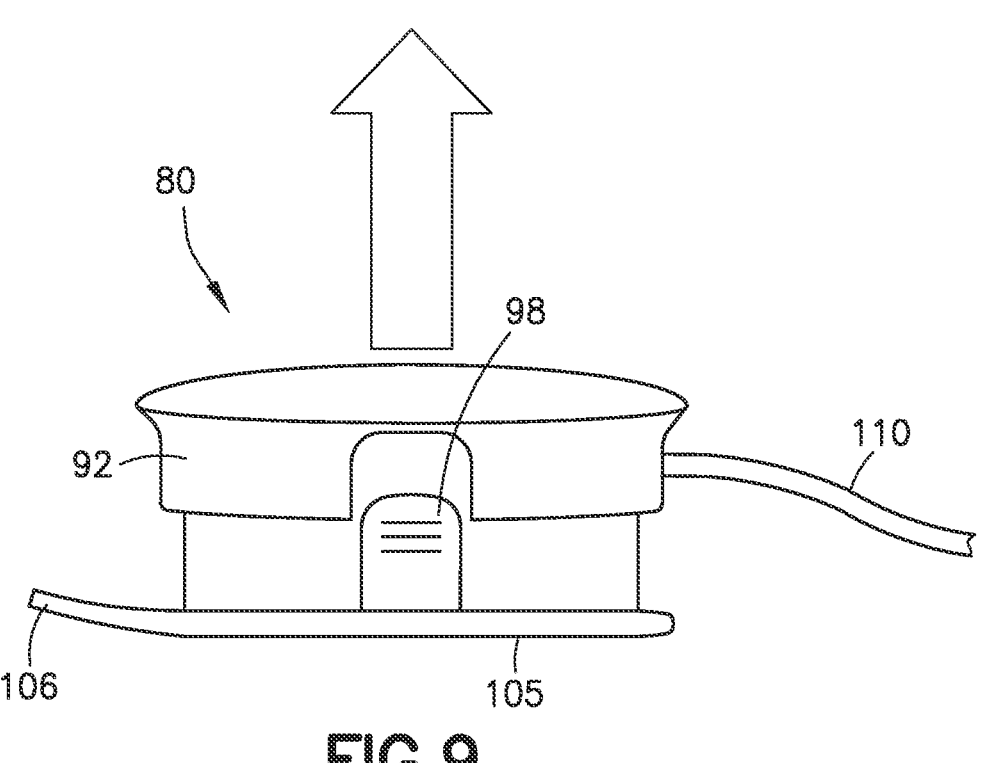
FIG. 9 is a front view of the needle hub of FIG. 7, showing a cannula withdrawal.

Referring to FIGS. 3-6D, according to one aspect or embodiment, the insertion mechanism 16 includes a needle hub 30 separate from the housing 20. The needle hub 30 includes a removal tab 32, an activation button 34, a status indicator 36, a finger grip, side grips, and an integrated cannula withdrawal tab 38. The needle hub 30 includes an in-dwelling cannula. The status indicator 36 may be white when unused (FIG. 4A), blue when the needle has been inserted and ready to infuse (FIG. 4B), and green when the cannula has been withdrawn (FIG. 4C). As shown in FIG. 5, the needle hub 30 is used by removing the packaging, removing an adhesive liner from the bottom of the needle hub 30, attaching the needle hub 30 to a skin surface, and squeezing the activation button 34, which causes the needle to automatically retract leaving an in-dwelling cannula in the patient. The medicament or fluid is then infused into the patient. Once the infusion is complete, the cannula withdrawal tab 38 is pulled, which retracts the cannula. The needle hub 30 can then be removed from the skin of the patient.

Referring to FIGS. 6A-6D, in one aspect or embodiment, the needle hub 30 includes a hub body 42, the activation button 34, a needle holder 44, a needle 46 attached to the needle holder 44, a needle spring 48, a cannula holder 50, a cannula 52 attached to the cannula holder 50, and a cannula spring 54. The activation button 34 is moveable relative to the hub body 42 and has a first actuation surface 56. The needle holder 44 is moveable relative to the hub body 42 and has a second actuation surface 58. The first actuation surface 56 of the activation button 34 is configured to engage the second actuation surface 58 of the needle holder 44. The needle spring 48 biases the needle holder 44 to a retracted position where the needle 46 is positioned within the hub body 42. The cannula holder 50 is moveable relative to the hub body 42 and the needle holder 44. The cannula 52 is configured to be in fluid communication with a fluid source, such as the fluid reservoir 12. The cannula spring 54 biases the cannula holder 50 to a retracted position where the cannula 52 is positioned within the hub body 42. Movement of the activation button 34 is configured to cause the first actuation surface 56 of the activation button 34 to engage the second actuation surface 58 of the needle holder 44 to move the needle holder 44 and the cannula holder 50 from the respective retracted positions to insertion positions where distal ends of the needle 46 and the cannula 52 are positioned outside of the hub body 42, with the needle holder 44 configured to return to the retracted position while the cannula holder 50 remains in the insertion position. Movement of a portion of the hub body 42 is configured to disengage a connection between the cannula holder 50 and the hub body 42 to allow the cannula holder 50 to return to the retracted position.

Referring again to FIGS. 6A-6D, the needle holder 44 includes a passageway 60 configured to be in fluid communication with the fluid reservoir 12, with the needle 46 in fluid communication with the passageway 60 of the needle holder 44. At least a portion of the needle 46 is received within the cannula 52. Fluid is configured to flow from the fluid reservoir 12 via tubing 62 to the passageway 60 of the needle holder 44, through the needle 46, and into the cannula 52. The cannula holder 50 includes a seal 64 engaged with the needle 46. The needle hub 30 includes a first projection 66 and the cannula holder 50 includes a second projection 68, with the first projection 66 of the needle hub 66 engaging the second projection 68 of the cannula holder 50 when the cannula 52 is in the insertion position to restrict movement of the cannula holder 50 to the retracted position.

Referring to FIGS. 3-6D, the needle hub 30 includes a removal tab 70, where movement of the removal tab 70 releases an engagement between the first projection 66 of the needle hub 30 and the second projection 68 of the cannula holder 50 to allow the cannula spring 54 to bias the cannula 52 to the retracted position. At least a portion of the removal tab 70 is configured to be engaged with a skin surface of a person after attaching the needle hub 30 to a person. The activation button 34 is moveable along a first axis 72, and the needle holder 44 and the cannula holder 50 are moveable along a second axis 74 perpendicular to the first axis 72. The first actuation surface 56 of the activation button 34 is configured to disengage from the second actuation surface 58 of the needle holder 44 after movement of the activation button 34 a predetermined distance along the first axis 72.

Figure 10:
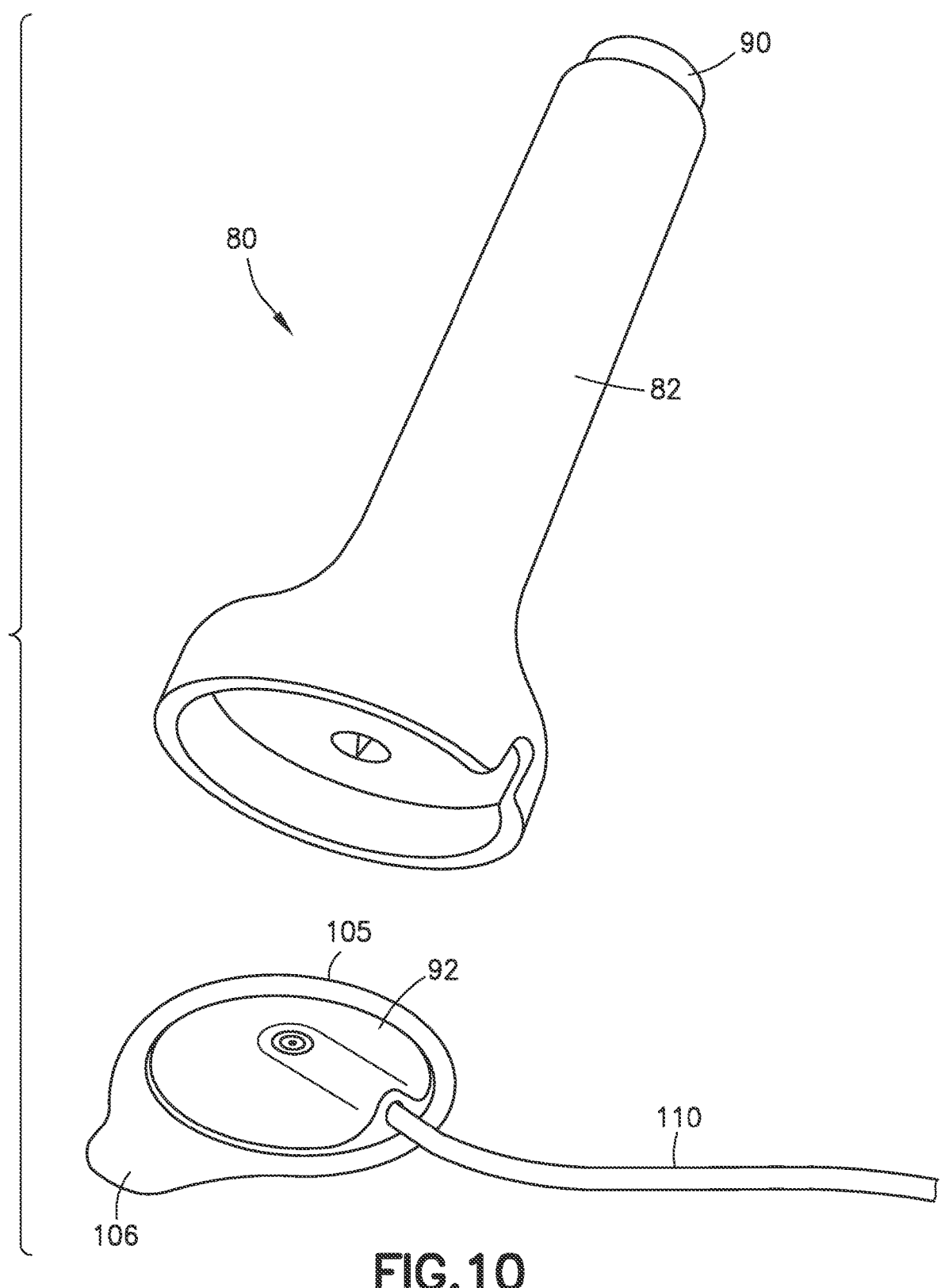
FIG. 10 is a perspective view of a needle hub according to a further aspect or embodiment of the present application.

Referring to FIG. 7-14, a needle hub 80 according to a further aspect or embodiment includes an applicator 82 having a needle holder 84, a needle 86 attached to the needle holder 84, a needle retraction spring 88, and an activation button 90, and a hub body 92 having a cannula holder 94, a cannula 96 attached to the cannula holder 94, a cannula withdrawal button 98, and a cannula retraction spring 100. At least a portion of the hub body 92 is configured to be received within the applicator 82 and the applicator 82 is configured to be separated from the hub body 92. Movement of the activation button 90 is configured to move the needle holder 84 and the cannula holder 94 from a retracted position, where the needle 86 and the cannula 96 are positioned within the applicator 82 or hub body 92, to an insertion position, where distal ends of the needle 86 and the cannula 96 are positioned outside of the applicator 82 and the hub body 92. The cannula withdrawal button 98 locks the cannula holder 94 in the insertion position against a biasing force of the cannula retraction spring 100 when the cannula holder 94 is moved from the retracted position to the insertion position. As shown in FIG. 10, in one aspect or embodiment, the cannula withdrawal button 98 may be omitted.

Referring to FIGS. 12A-12F, the needle holder 84 is configured to move to the retracted position after movement of the cannula holder 94 to the insertion position. The activation button 90 includes an extension 102 having a drive protrusion 103 and the applicator 82 includes a drive surface 104 configured to engage the drive protrusion 103. Upon movement of the activation button 90, the drive protrusion 103 engages the needle holder 84 to move the needle holder 84 and the cannula holder 94 to the insertion position, with the drive protrusion 103 engaging the drive surface 104 of the applicator 82 to move the extension 102 radially outward thereby releasing the needle holder 84 from the drive protrusion 103 to allow the needle retraction spring 100 to return the needle holder 84 to the retracted position. Actuation of the cannula withdrawal button 98 is configured to move the cannula holder 94 from the insertion position to the retracted position. The hub body 92 further includes an adhesive pad 105 configured to secure the hub body 92 to a skin surface of a person. The adhesive pad 105 includes a removal tab 106 extending radially outward from the hub body 92. The activation button 90 is received within an opening 107 defined by a body 108 of the applicator 82. The cannula holder 94 includes a port 109 configured to be in fluid communication with the fluid reservoir 12, with the cannula 96 in fluid communication with the port 109. Tubing 110 is connected to the port of the cannula holder 94.

Figure 11:
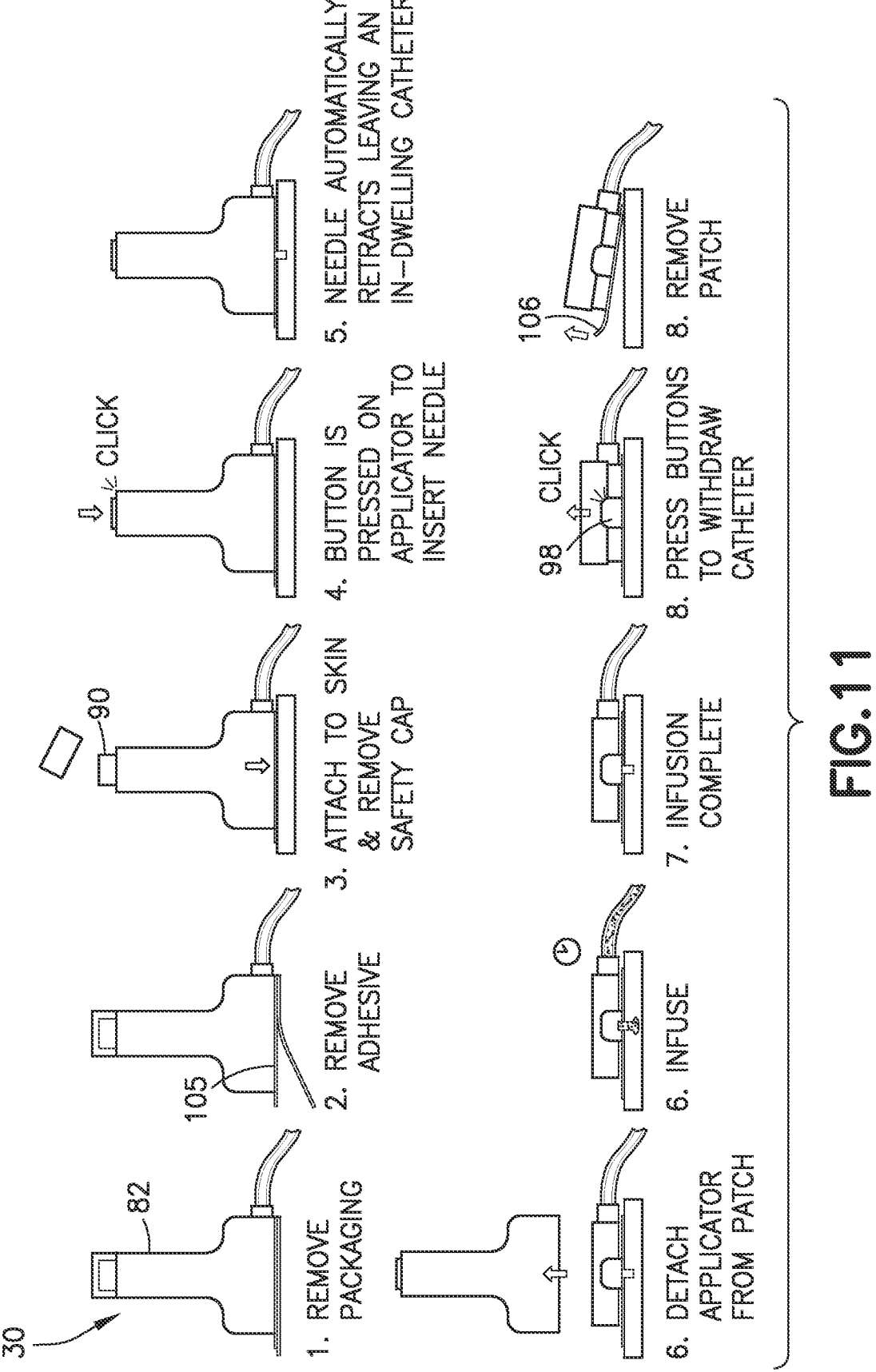
FIG. 11 is a schematic view showing a method of using the needle hub of FIG. 7.
Figures 12A, 12B, 12C:
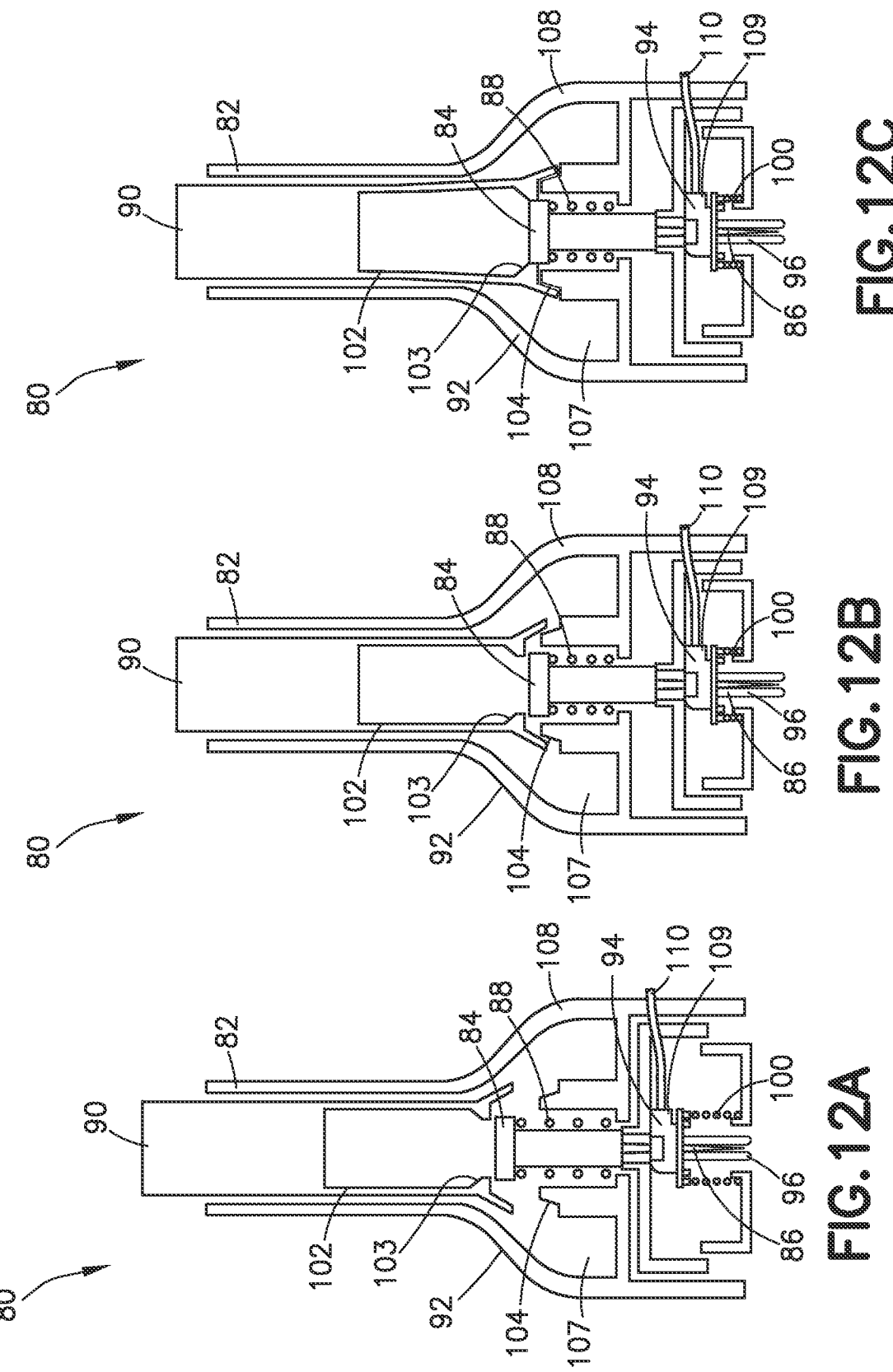
FIG. 12A is a schematic view of the needle hub of FIG. 7, showing a pre-use position of the needle hub.
FIG. 12B is a schematic view of the needle hub of FIG. 7, showing the needle hub being actuated.
FIG. 12C is a schematic view of the needle hub of FIG. 7, showing a needle being retracted.
Figures 12D, 12E, 12F:
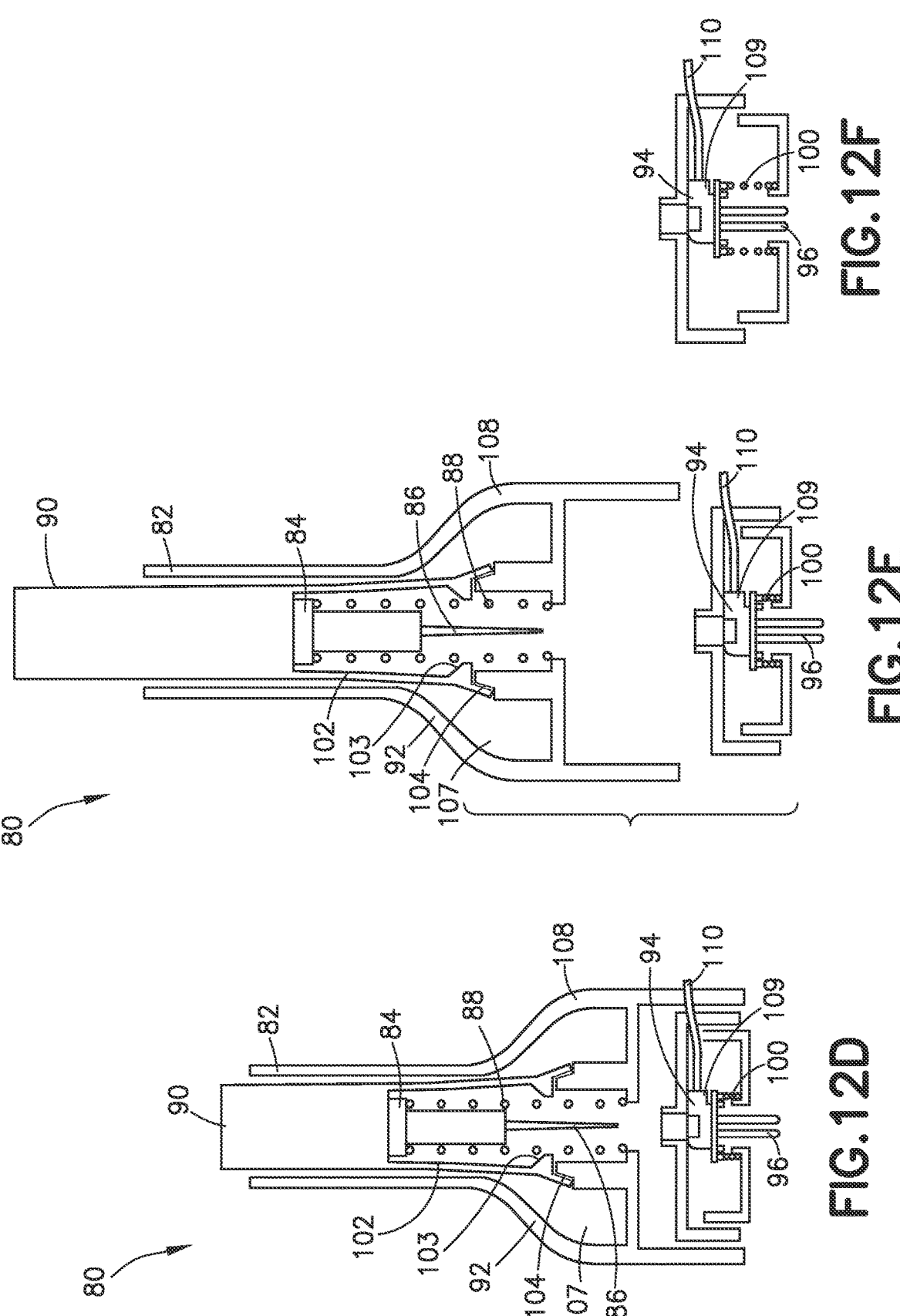
FIG. 12D is a schematic view of the needle hub of FIG. 7, showing a needle in a retracted position.
FIG. 12E is a schematic view of the needle hub of FIG. 7, showing an applicator being detached from the needle hub.
FIG. 12F is a schematic view of the needle hub of FIG. 7, showing a cannula in a retracted position.

Referring to FIG. 11, in one aspect or embodiment, the needle hub 80 is used by removing the packaging, removing an adhesive liner, attaching the needle hub 80 to a skin surface of a patient and removing a safety cap, and pressing the activation button 90 of the applicator 82, which automatically actuates and retracts the needle 86 to leave the in-dwelling cannula 96. The applicator 82 can then be removed from the hub body 92 and the infusion can commence. Once the infusion is complete, the cannula withdrawal button 98 may be pressed to remove the cannula 96 from the patient, with the hub body 92 being removed from the skin of the patient using the removal tab 106.

Figures 13, 14:
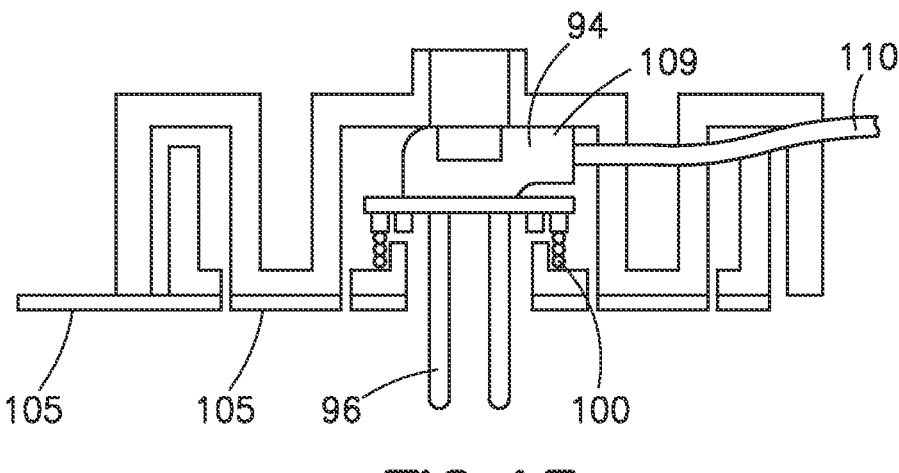
FIG. 13 is a cross-sectional view of a needle hub according to a further aspect or embodiment of the present application.
FIG. 14 is a cross-sectional view of the needle hub of FIG. 13.
Figure 15:
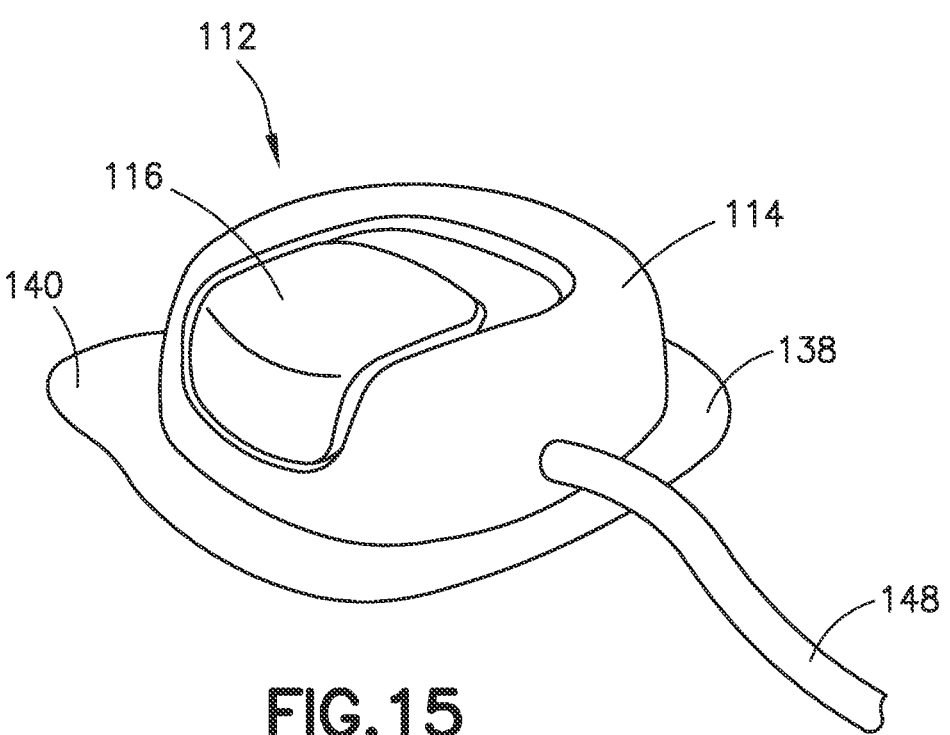
FIG. 15 is a perspective view of a needle hub according to a further aspect or embodiment of the present application.

Referring to FIGS. 13 and 14, in one aspect or embodiment, the cannula holder 94 includes a portion of the adhesive pad 105, which removes a portion of the adhesive pad 105 from the skin of the patient when the cannula holder 94 is removed from the hub body 92 to facilitate easier removal of the remainder of the adhesive pad 105 from the skin of the patient.

Figure 16:
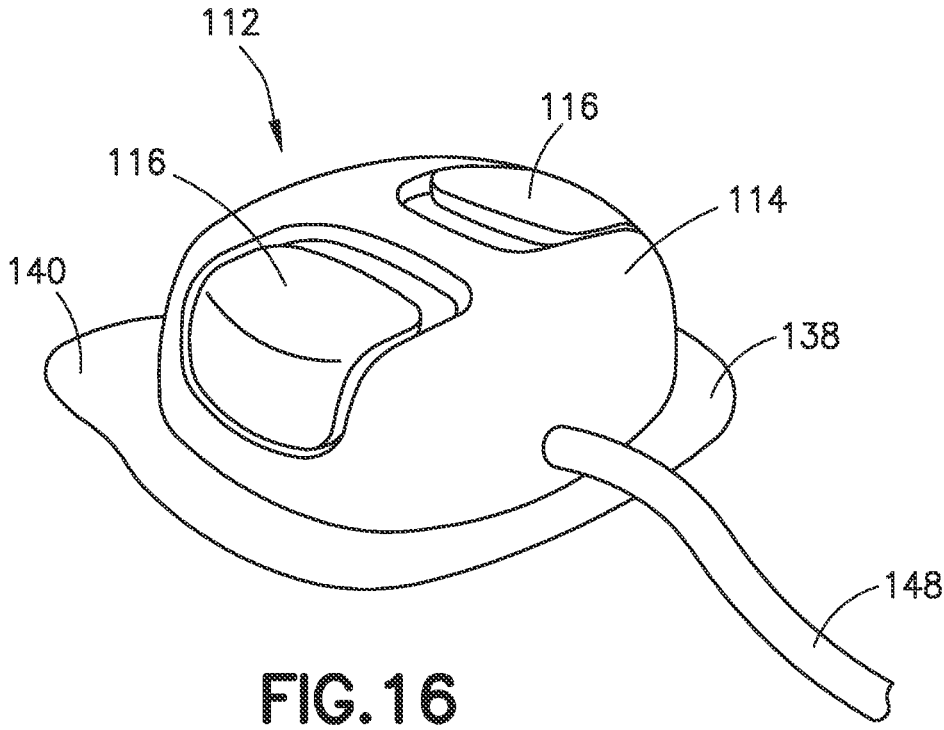
FIG. 16 is a perspective view of a needle hub according to a further aspect or embodiment of the present application.

Referring to FIGS. 15-18B, a needle hub 112, according to a further aspect or embodiment, includes a hub body 114, an activation button 116, a needle holder 118 and a needle 120 attached to the needle holder 118, a cannula holder 122 and a cannula 124 attached to the cannula holder 122, a needle actuation mechanism 126, and a cannula spring 128. The needle actuation mechanism 126 is configured to move the needle holder 118 and the cannula holder 122 from a retracted position to an insertion position and is configured to move the needle holder 118 back to the retracted position. The needle actuation mechanism 126 includes a cam track 130, a cam member 132 received within the cam track 130, and a torsion spring 134. The torsion spring 134 biases the cam member 132 relative to the cam track 130. The cannula spring 128 biases the cannula holder 122 to a retracted position. Movement of the activation button 116 is configured to cause the needle holder 118 and the cannula holder 122 to move from the retracted position to the insertion position, with the needle holder 118 configured to return to the retracted position while the cannula holder 122 remains in the insertion position. As shown in FIG. 16, in one aspect or embodiment, the needle hub 112 includes two lateral activation squeeze buttons 116. The needle hub 112 is used in the same manner as described above in connection with the needle hub 30 shown in FIG. 5.

Figure 17:
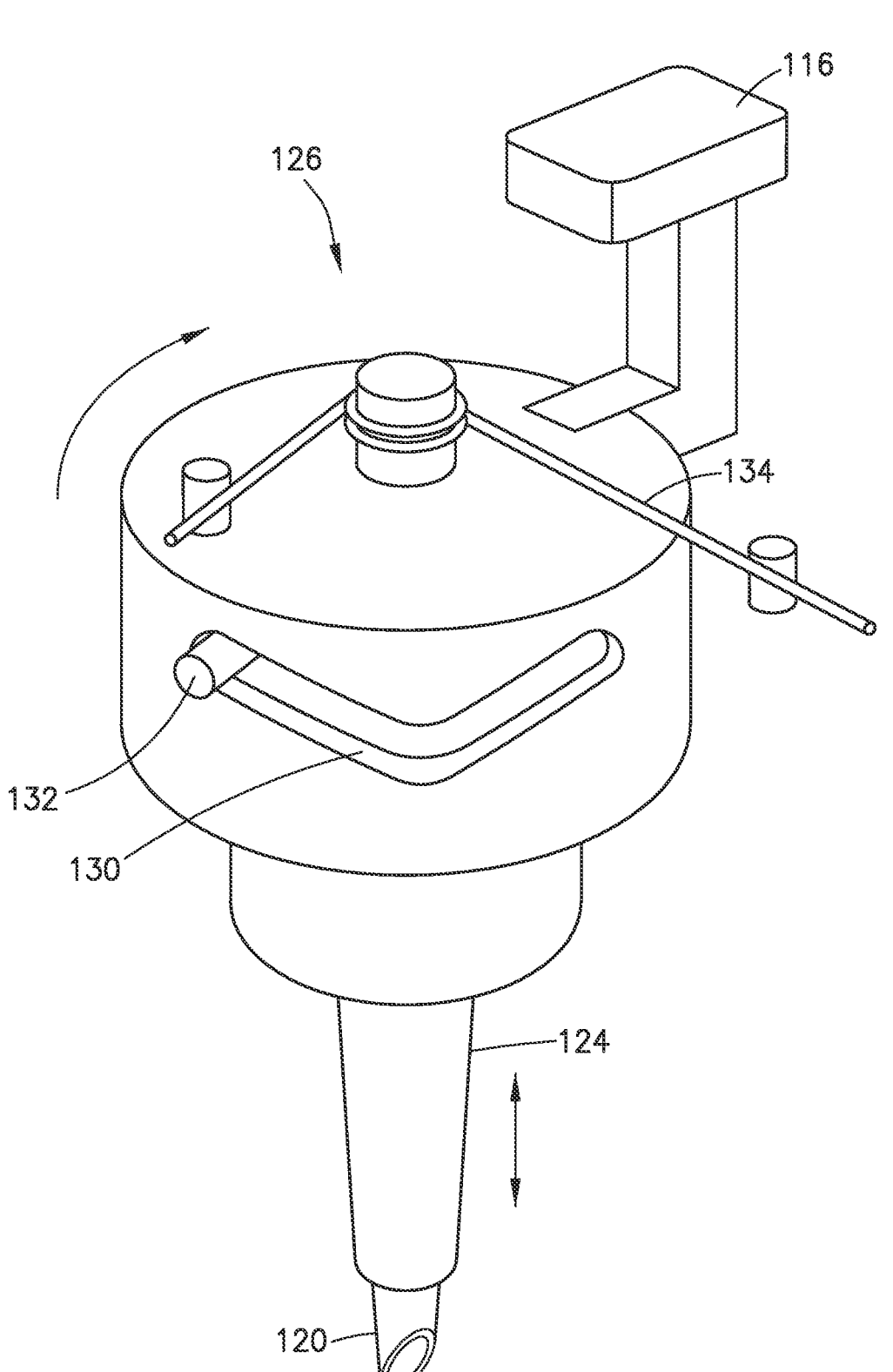
FIG. 17 is a perspective view of a needle actuation assembly according to one aspect or embodiment of the present application.
Figure 18A:
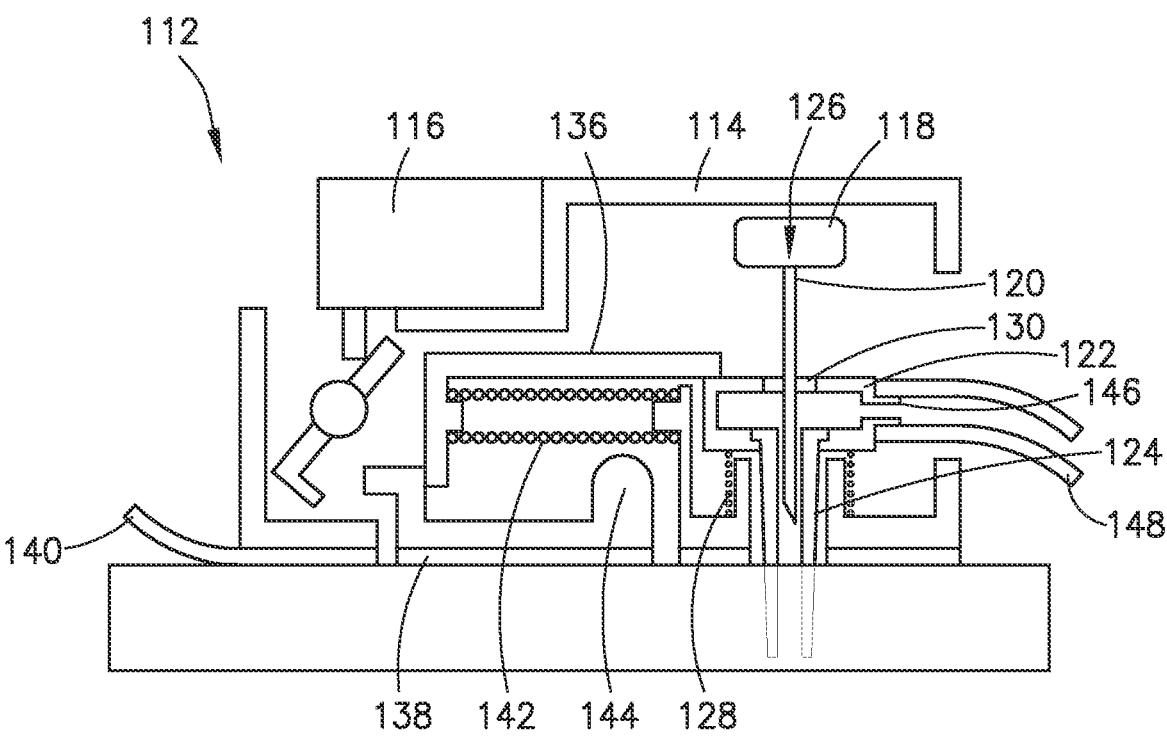
FIG. 18A is a cross-sectional view of the needle hub of FIG. 15, showing a cannula insertion position.
Figure 18B:
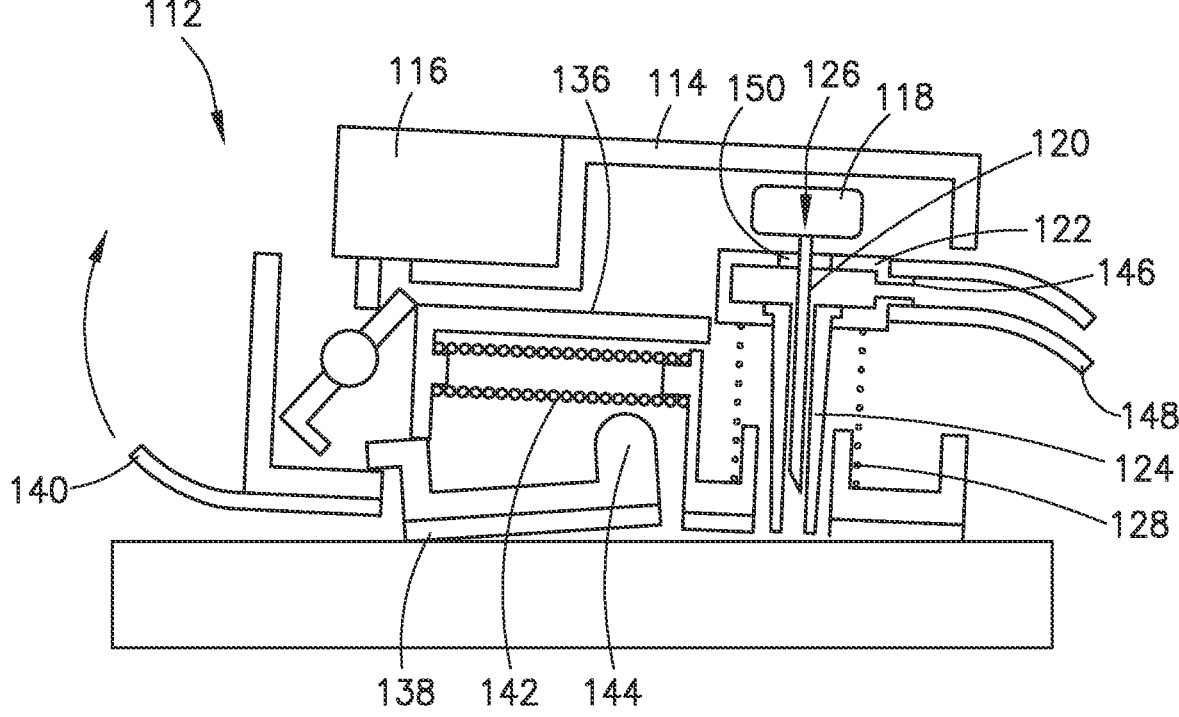
FIG. 18B is a cross-sectional view of the needle hub of FIG. 15, showing a cannula retraction position.

Referring to FIGS. 17-18B, the hub body 114 includes a cannula lock 136 configured to lock the cannula holder 122 in the insertion portion. The needle hub 112 includes an adhesive pad 138 configured to secure the hub body 114 to a skin surface of a person, with the adhesive pad 138 including a removal tab 140. Movement of the removal tab 140 is configured to disengage the cannula lock 136 and the hub body 114 to allow the cannula holder 122 to return to the retracted position. The cannula lock 136 is biased away from the cannula holder 122 via a lock spring 142, where the hub body 112 includes a hinged portion 144, with the hinged portion 144 configured to rotate upon movement of the removal tab 140 and disengage from the cannula lock 136. The cannula holder 122 includes a port 146 configured to be in fluid communication with the fluid reservoir 12, with the cannula 124 in fluid communication with the port 146. The needle hub 112 includes tubing 148 connected to the port 146 of the cannula holder 122. The cannula holder 122 includes a seal 150 engaged with the needle 120, with at least a portion of the needle 120 received within the cannula 124.

Figure 19:
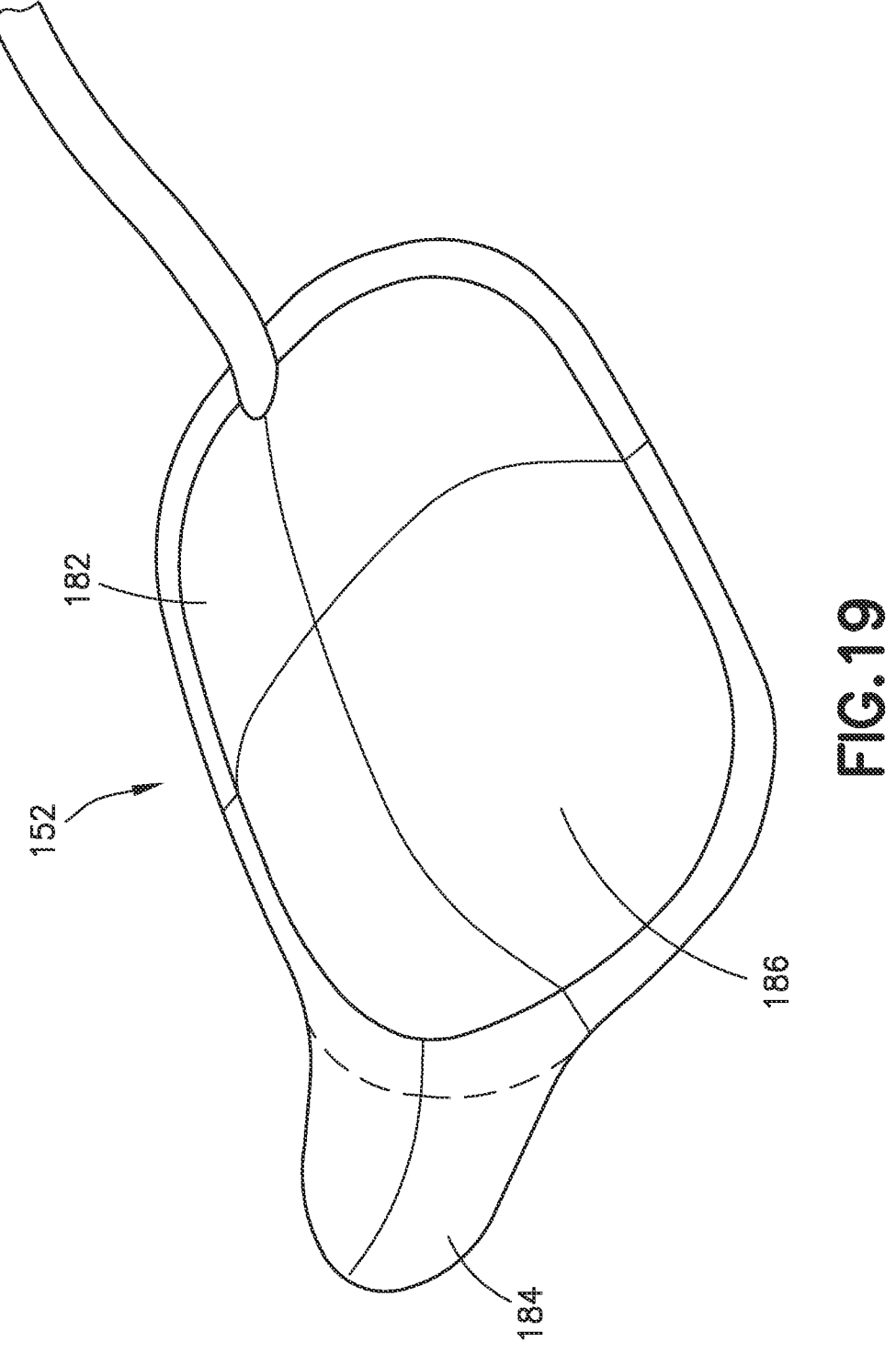
FIG. 19 is a perspective view of a needle hub according to a further aspect or embodiment of the present application.
Figure 20:
FIG. 20 is a schematic view showing a method of using the needle hub of FIG. 19.
Figure 21:
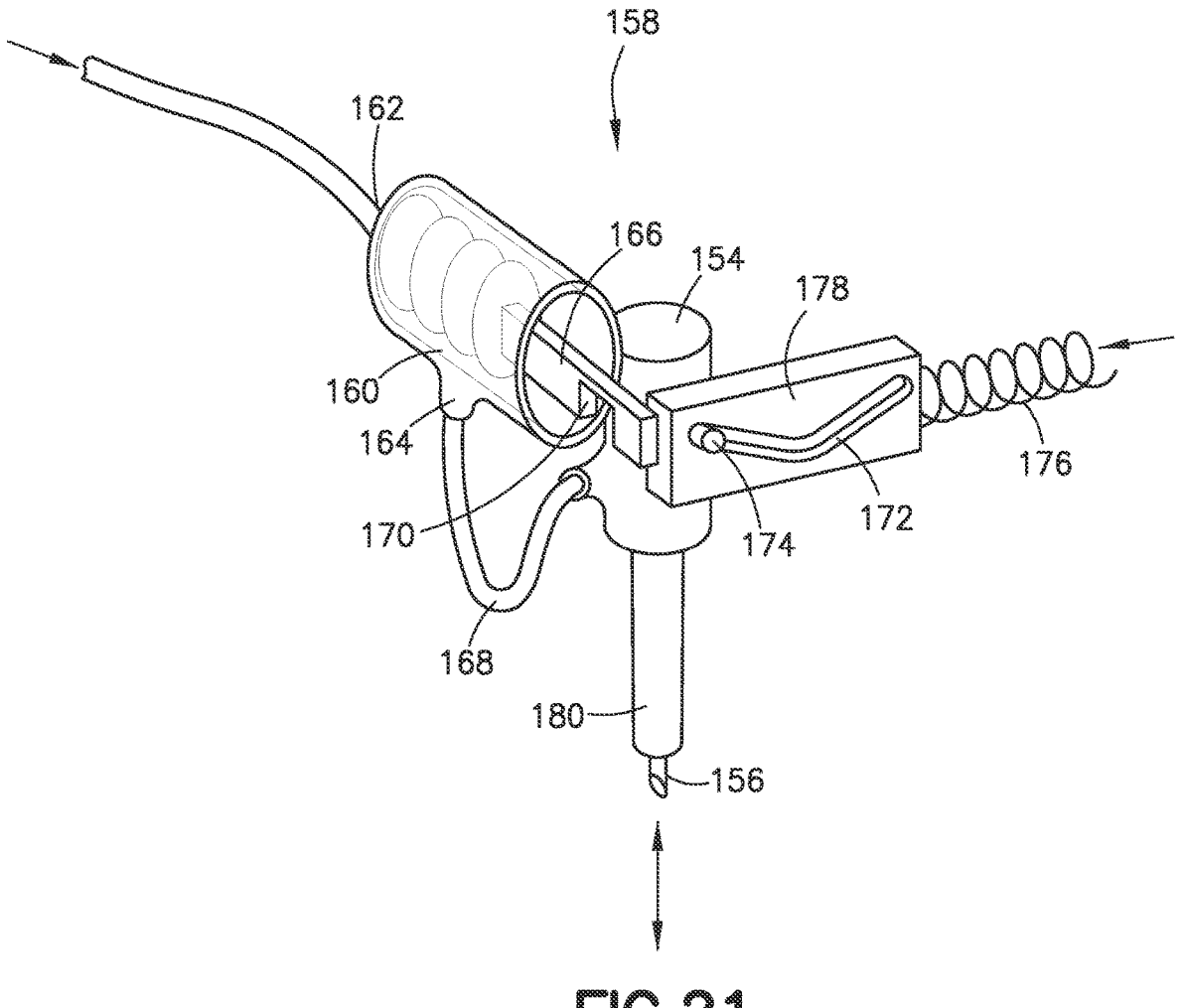
FIG. 21 is a perspective view of a needle actuation assembly according to a further aspect or embodiment of the present application.

Referring to FIGS. 19-21, a needle hub 152, according to a further aspect or embodiment, includes a needle holder 154 and a needle 156 attached to the needle holder 154, a needle actuation assembly 158 configured to move the needle holder 154 from a retracted position, to an insertion position, and back to the retracted position, and a pressure interlock 160 including an inlet 162 configured to be in fluid communication with the fluid reservoir 12, an outlet 164 in fluid communication with the needle 156, and a lock member 166. The lock member 166 has a first position where the lock member 166 prevents actuation of the needle actuation assembly 158 and a second position where the lock member 166 allows actuation of the needle actuation assembly 158. The lock member 166 is moved from the first position to the second position based on a pressure within the pressure interlock 160.

Referring to FIG. 21, the lock member 166 isolates the inlet 162 from the outlet 164 when the lock member 166 is in the first position, and the lock member 166 allows fluid communication between the inlet 162 and the outlet 164 when the lock member 166 is in the second position. The needle hub 152 further includes tubing 168 connected to the outlet 164 and in fluid communication with the needle 156. The lock member 166 includes an opening 170, with a portion of the needle actuation assembly 158 extending through the opening 170 of the lock member 166 when the lock member 166 is in the second position. The needle actuation assembly 158 includes a cam track 172, a cam member 174, and an actuation spring 176 biasing the cam member 174 relative to the cam track 172. A cam block 178 defines the cam track 172, with the cam block 178 extending through the opening 170 of the lock member 166 when the lock member 166 is in the second position. The needle actuation assembly 158 further includes a cannula 180, where the needle 156 is received within the cannula 180 when the needle holder 156 is in the retracted position.

Referring again to FIGS. 19-21, the needle hub 152 includes a housing 182 and a removal tab 184. A top surface 186 of the housing 182 is smooth and free of activation buttons. As shown in FIG. 20, the needle hub 152 is used by removing packaging, removing an adhesive liner, attaching the needle hub 152 to a skin surface of a patient, and activating the drive mechanism 27 to insert the needle 156, with the needle 156 automatically retracting leaving the in-dwelling cannula 180. After infusion is complete, the needle hub 152 is removed by grasping the removal tab 184 and lifting upwards, with the cannula 180 automatically retracting. In one aspect or embodiment, pulling the removal tab 184 causes a drop in pressure of the pressure interlock 160 to cause the cannula holder and/or the cannula 180 to automatically retract.

Referring to FIGS. 22-25, a drug delivery device 190 and a needle hub 192, according to a further aspect or embodiment, is shown. The drug delivery device 190 may be similar to the drug delivery device 10 shown in FIGS. 1 and 2. The drug delivery device 190 and the needle hub 192 of FIGS. 22-25, however, is modular, with the needle hub 192 optionally integrated within the drug delivery device 190 (FIG. 24) or with the needle hub 192 separated from the drug delivery device 190 and separately attached to a skin surface of a patient (FIG. 25). In one aspect or embodiment, the drug delivery device 190 and the needle hub 192 may remain connected or integral for lower drug volume and separated with a fluid connection therebetween for larger drug volumes.

Figures 26A, 26B, 26C:
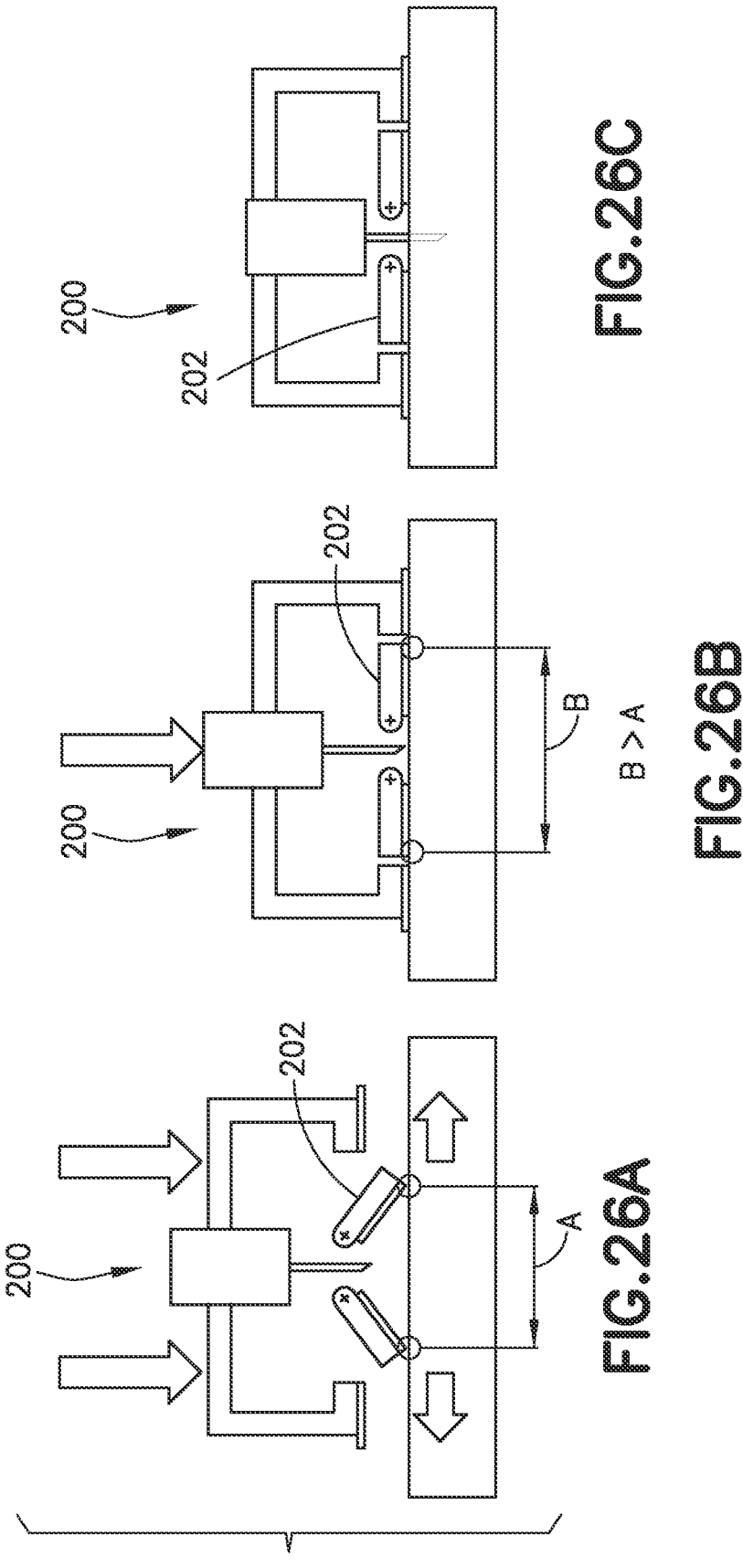
FIG. 26A is a cross-sectional view of a needle hub according to a further aspect or embodiment of the present application, showing an initial position of the needle hub.
FIG. 26B is a cross-sectional view of a needle hub according to a further aspect or embodiment of the present application, showing engagement with a skin surface.
FIG. 26C is a cross-sectional view of a needle hub according to a further aspect or embodiment of the present application, showing insertion of a needle.

Referring to FIGS. 26A-26C, a needle hub 200 with a skin tenting reduction feature, according to one aspect or embodiment, is shown. The needle hub 200 includes a rotating engagement mechanism 202, with a portion of the rotating engagement mechanism 202 first contacting a skin surface of the patient and adhering to the skin surface and further rotating as the needle hub 200 is fully pressed onto the skin surface. The initial adherence and further rotation of the rotating engagement mechanism stretches the skin to reduce skin tenting.

Referring to FIGS. 27A-27C, a needle hub 204 with a skin tenting reduction feature according to one aspect or embodiment is shown. The needle hub 204 includes an adhesive ring 206 that is pressed onto the skin prior to insertion of a needle when an activation button is depressed or actuated. The adhesive ring 206 stretches the skin to reduce skin tenting.

Figures 28A, 28B, 28C:
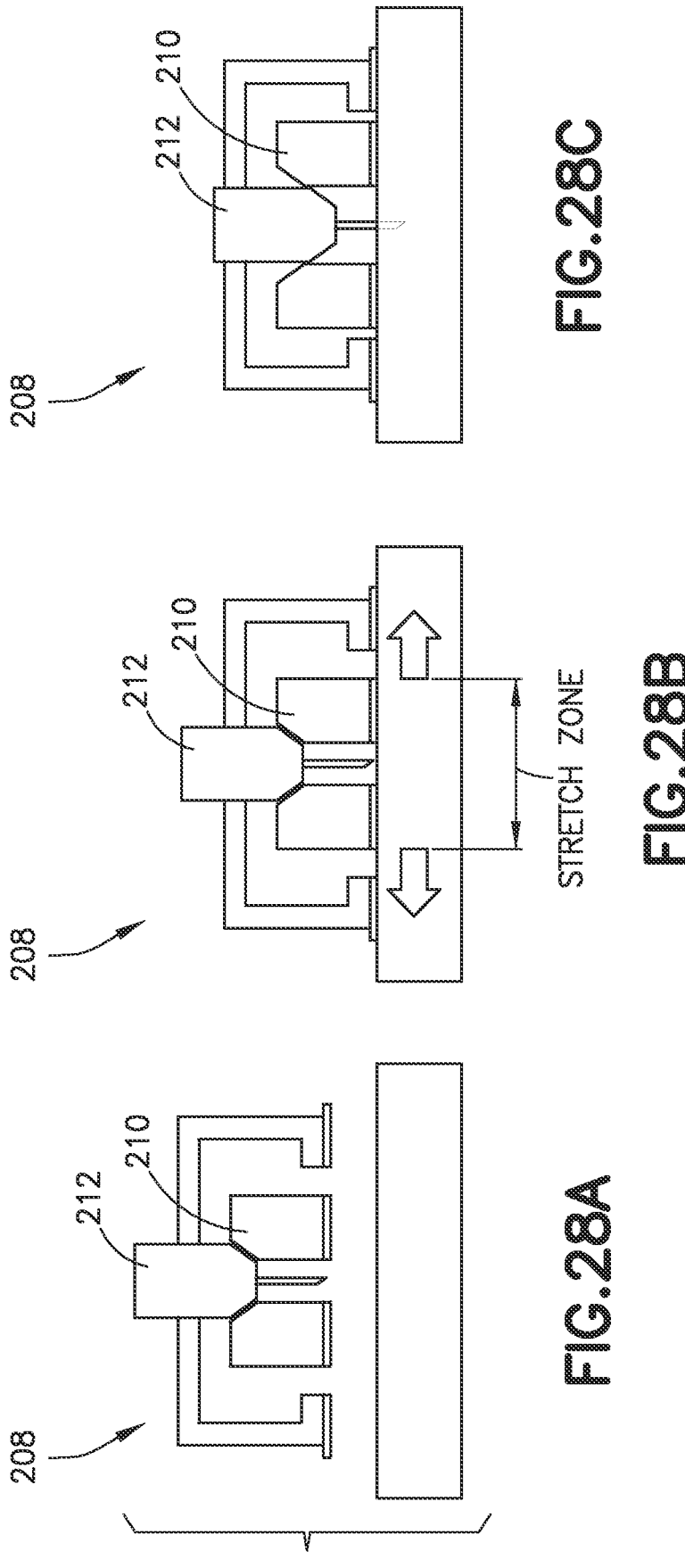
FIG. 28A is a cross-sectional view of a needle hub according to a further aspect or embodiment of the present application, showing an initial position of the needle hub.
FIG. 28B is a cross-sectional view of a needle hub according to a further aspect or embodiment of the present application, showing engagement with a skin surface.
FIG. 28C is a cross-sectional view of a needle hub according to a further aspect or embodiment of the present application, showing insertion of a needle.
Figure 30:
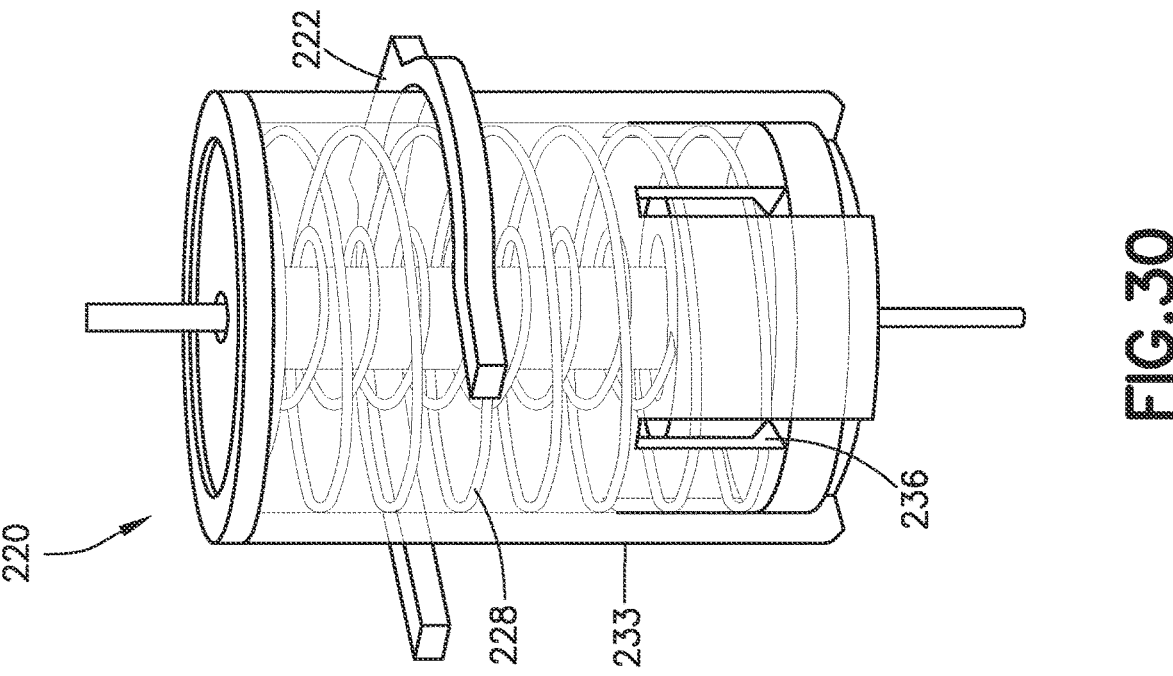
FIG. 30 is a perspective view of the needle actuation assembly of FIG. 29, showing an actuated position.
Figure 29:
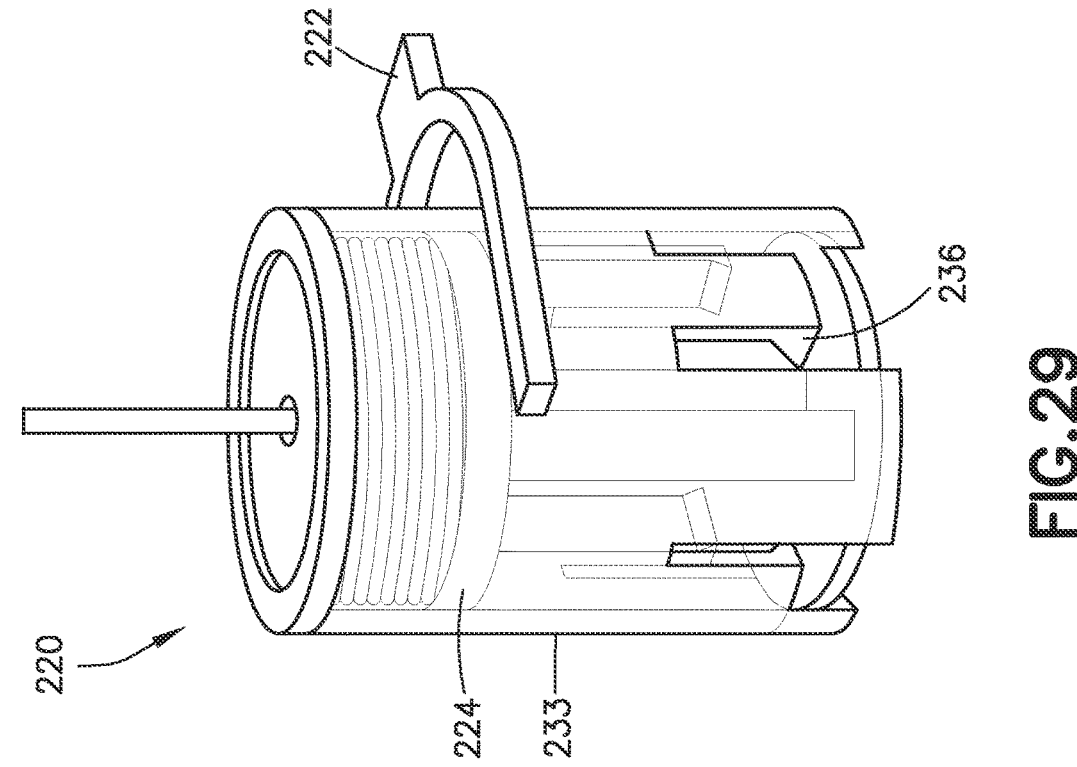
FIG. 29 is a perspective view of a needle actuation assembly according to a further aspect or embodiment of the present application, showing an unactuated position.
Figure 32:
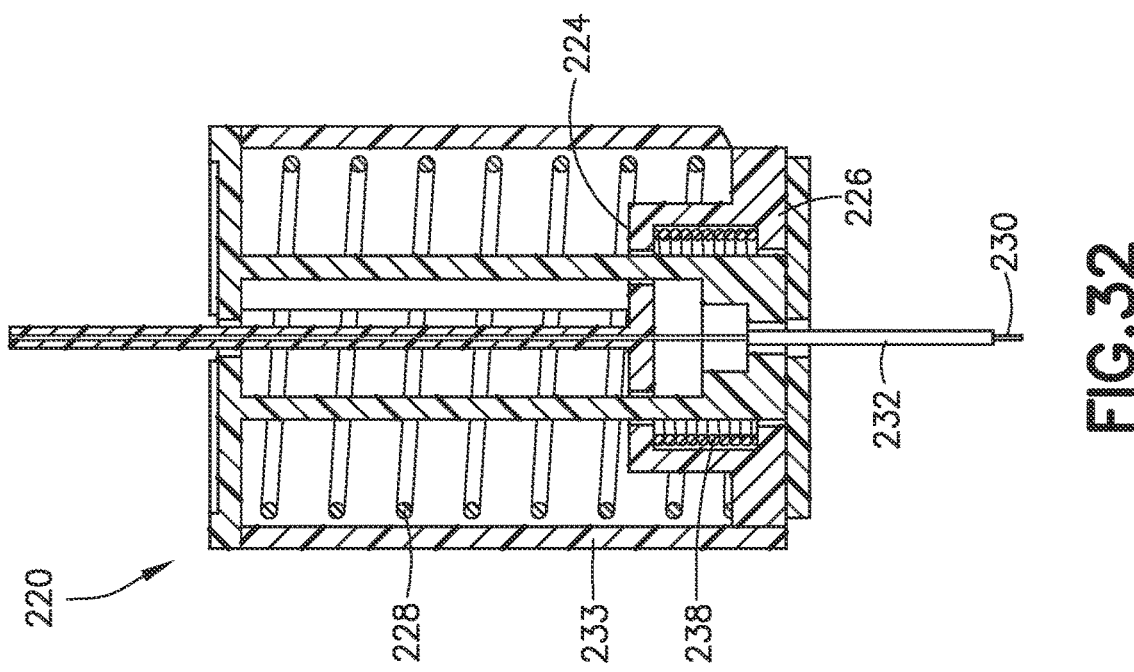
FIG. 32 is a cross-sectional view of the needle actuation assembly of FIG. 29, showing an actuated position.
Figure 31:
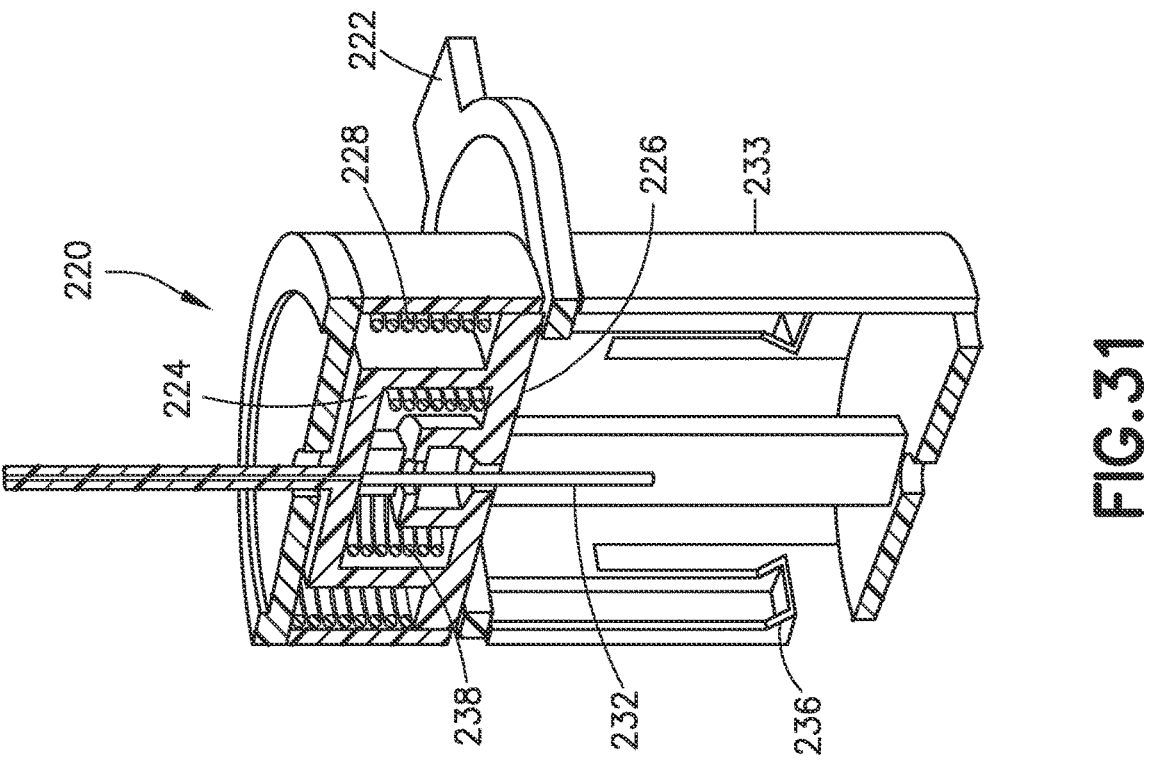
FIG. 31 is a cross-sectional view of the needle actuation assembly of FIG. 29, showing an unactuated position.
Figure 33:
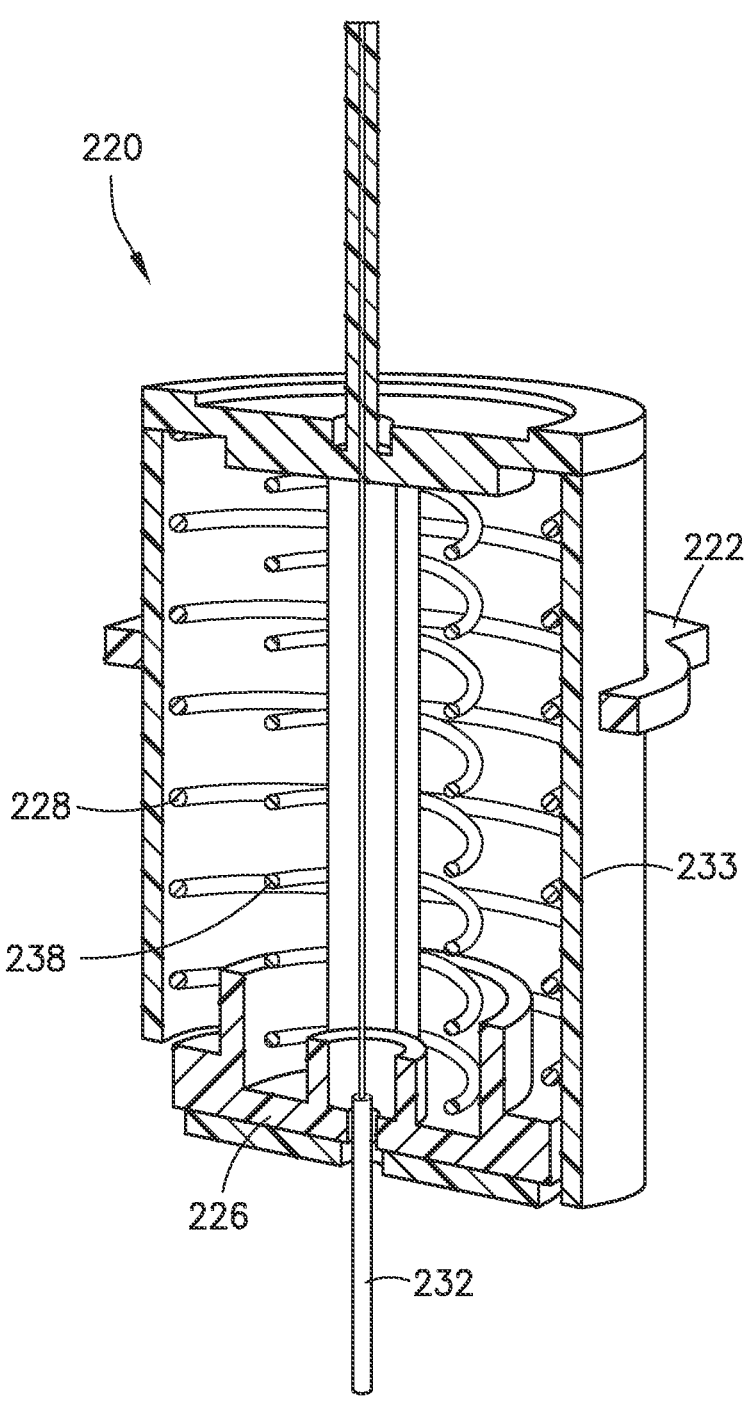
FIG. 33 is a cross-sectional view of the needle actuation assembly of FIG. 29, showing a retracted position.

Referring to FIGS. 28A-28C, a needle hub 208 with a skin tenting reduction feature according to one aspect or embodiment is shown. The needle hub 208 includes skin stretching member 210 that is moved radially outward after being initially adhered to a skin surface of a patient. An activation button 212 engages the skin stretching member 210 to move the skin stretching member 210 radially outward, which stretches the skin locally to reduce skin tenting.

The skin tenting reduction features and associated mechanisms of FIGS. 26A-28C may be incorporated into any of the aspect or embodiments of the needle hub or needle insertion arrangements disclosed herein.

Referring to FIGS. 29-33, a needle actuation assembly 220, according to one aspect or embodiment, includes a clip 222 that holds a needle actuator body 224 and cannula body 226 in the retracted position, which are biased by a spring 228. Pushing the clip 222 inwards releases the needle actuator body 224 and cannula body 226 to cause insertion of a needle 230 and a cannula 232. When the cannula body 226 reaches the bottom of a housing 233, the cannula body 226 contacts angled features causing the cannula body 226 to rotate and/or twist. The cannula body 226 is held down by clips 236 in the walls of the housing 233. After the cannula body 226 rotates and/or twists, the needle actuator body 224 is released and a return spring 238 retracts the needle 230.

Figure 34:
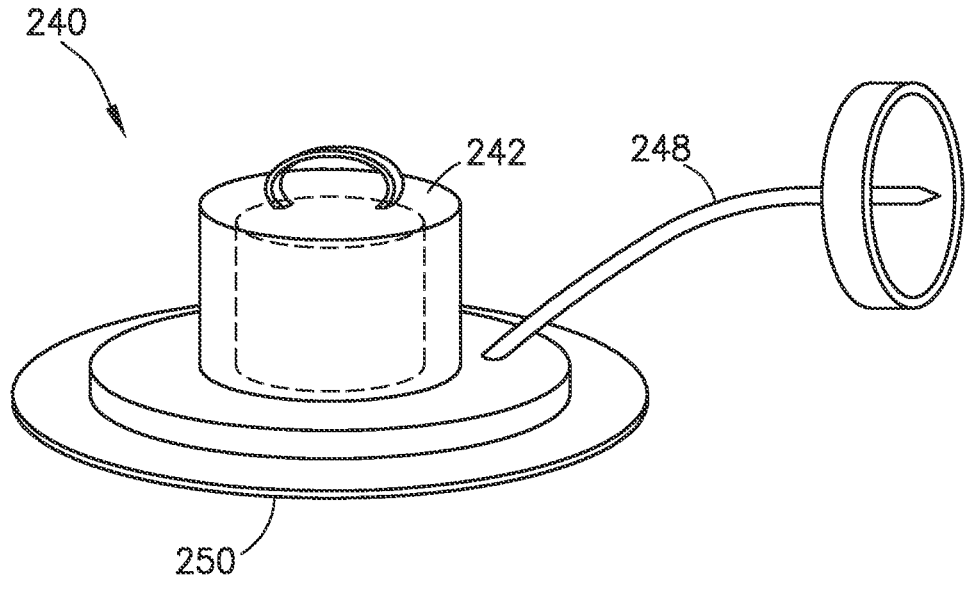
FIG. 34 is a perspective view of a needle hub according to a further aspect or embodiment of the present application.
Figure 35:
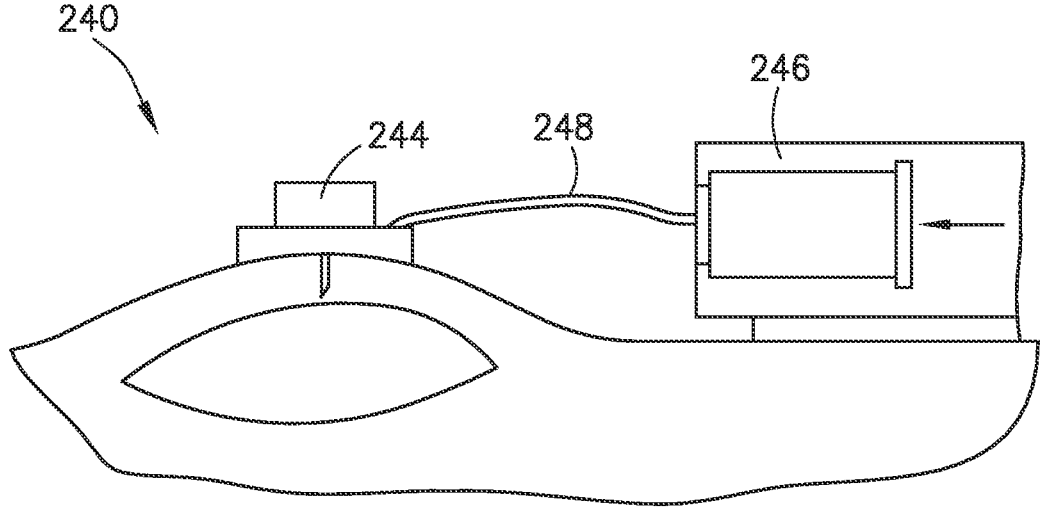
FIG. 35 is a schematic view of the needle hub of FIG. 34.
Figure 37:
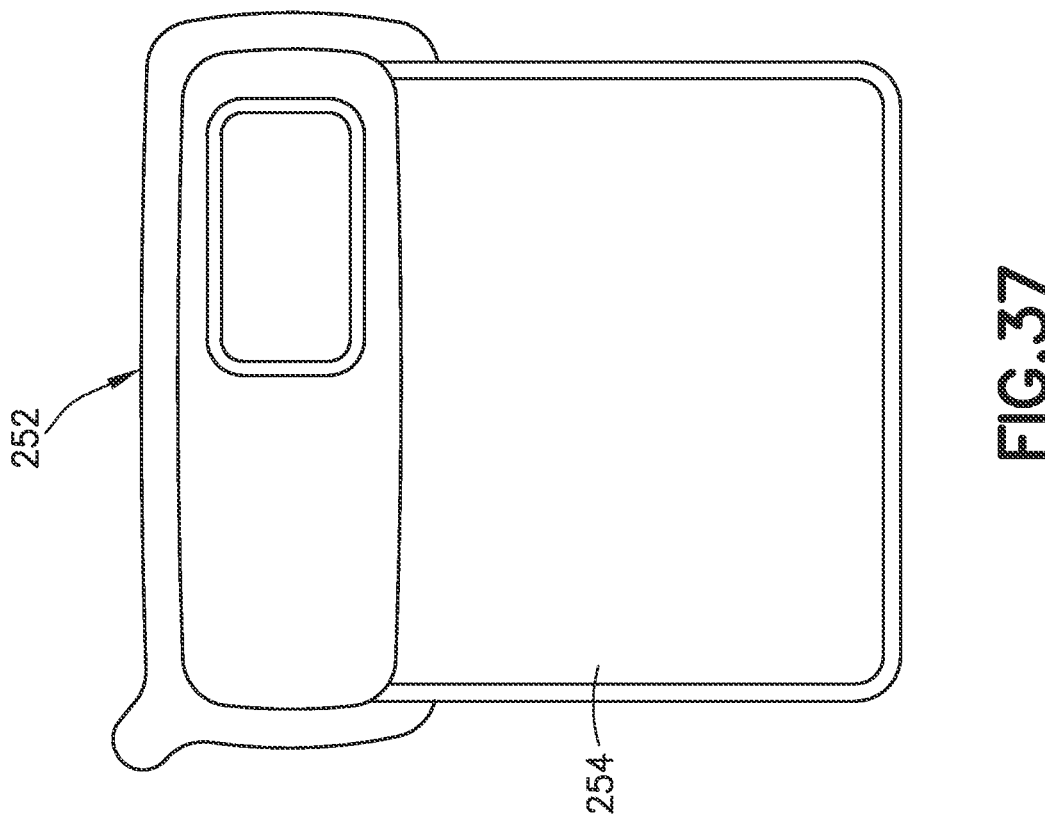
FIG. 37 is a front view of the drug delivery device of FIG. 36.
Figure 36:
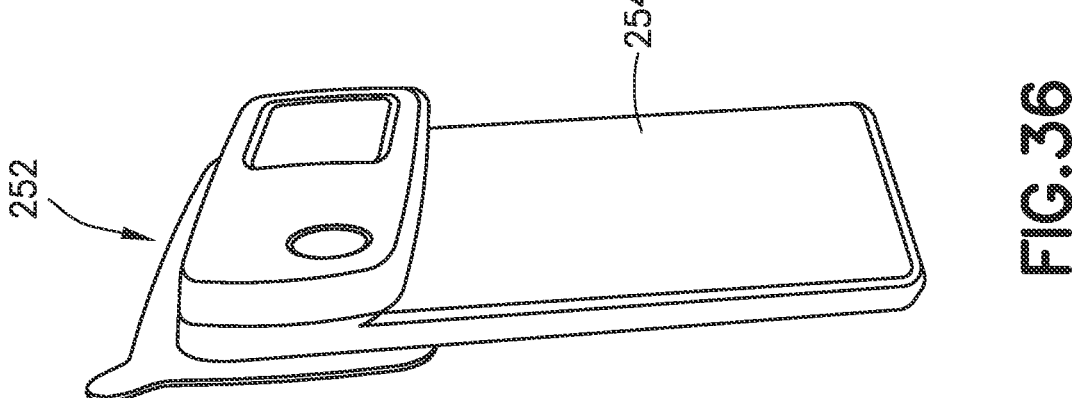
FIG. 36 is a perspective view of a drug delivery device according to a further aspect or embodiment of the present application.

Referring to FIGS. 34 and 35, a needle hub 240 according to a further aspect or embodiment is configured to be decoupled from remaining components of a drug delivery device. The needle hub 240 includes a protective cap 242, a needle insertion mechanism 244, connection arrangement 246 configured to place the needle hub 240 in fluid communication with the reservoir 12 and the drive mechanism 27, a fluid path 248, and an adhesive pad and/or layer 250. The connection arrangement 246 may provide for aseptic connection between the needle hub 240 and the reservoir 12. The needle retraction may be manually activated or automatically activated via a triggering mechanism connected to an end of dose event and/or a wireless connection between the driving unit and the needle hub 240. The triggering mechanism may include a flexible rigid connection to plunger rod movement (totally or partially at the end of translation). The fluid path 248 and connection arrangement 246 is maintained sterile until the connection is established, with sterilization of the sub-system and reservoir.

Figure 39:
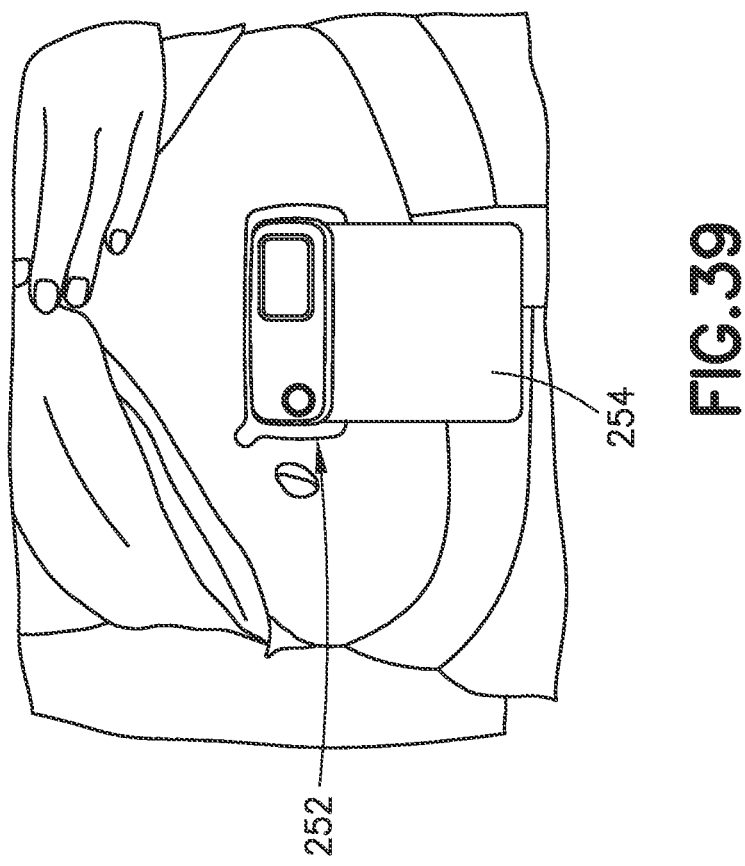
FIG. 39 is a front view of the drug delivery device of FIG. 36, showing the drug delivery device attached to a patient.
Figure 38:
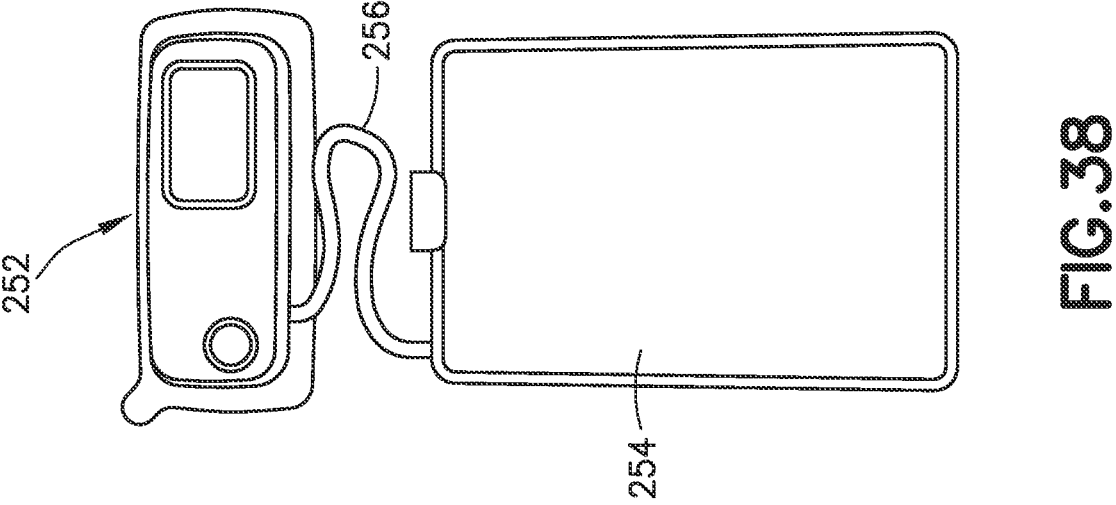
FIG. 38 is a front view of the drug delivery device of FIG. 36, showing a reservoir separated from the drug delivery device.

Referring to FIGS. 36-39, a drug delivery device 252, according to a further aspect or embodiment, includes a flexible reservoir 254, with at least a portion of the flexible reservoir 254 positioned externally from a remaining portion of the drug delivery device 252. The drug delivery device 252 may be similar to the drug delivery device 10 shown in FIGS. 1 and 2. As shown in FIG. 39, for smaller volumes, such as 10 mL-30 mL, the flexible reservoir 254 may be directly attached to the drug delivery device 252 and worn on a skin surface of the patient. As shown in FIG. 38, for larger volumes, such as 50 mL, the flexible reservoir 254 may be separated from the drug delivery device 252 and fluidly connected to the drug delivery device 252 via a fluid path 256, such as a tube. The flexible reservoir 254 may be separately attached to the patient via a belt clip, harness, strap, or other suitable arrangement.

Figure 40:
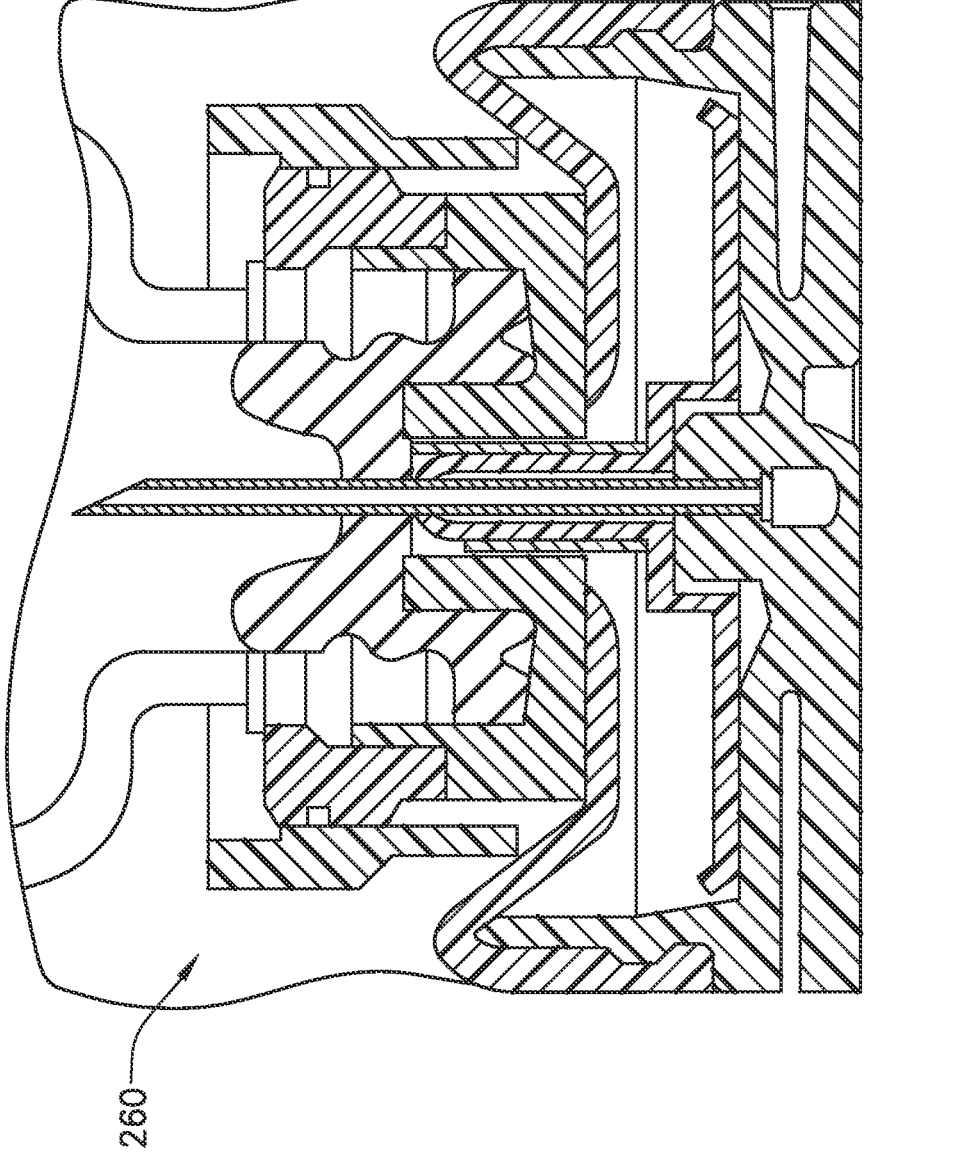
FIG. 40 is a partial cross-sectional view of a prior art valve assembly.
Figures 41, 42:
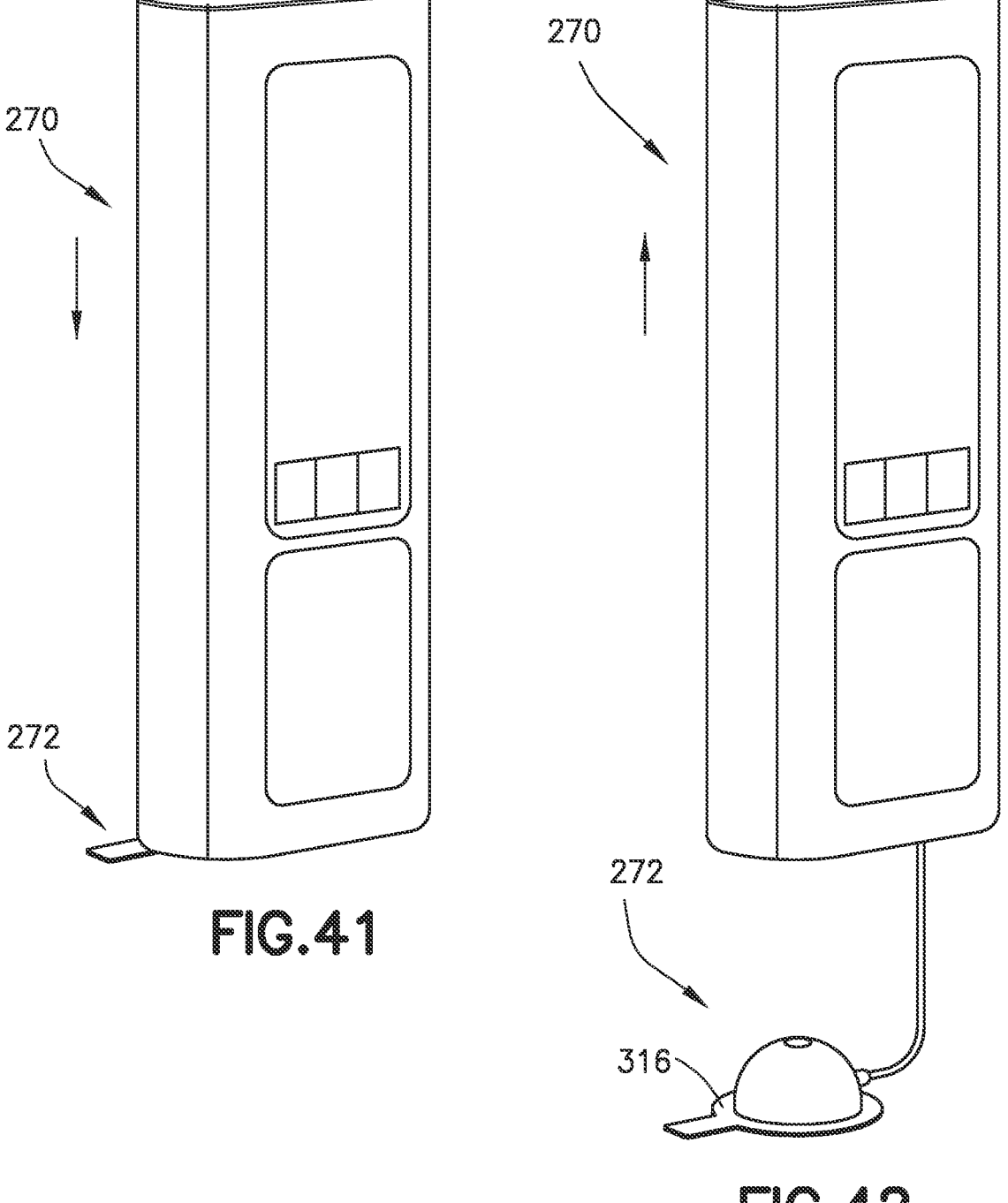
FIG. 41 is a perspective view of a drug delivery device and a needle hub according to a further aspect or embodiment of the present application, showing the needle hub positioned within the drug delivery device.
FIG. 42 is a perspective view of the drug delivery device and the needle hub of FIG. 41, showing the needle hub separated from the drug delivery device.
Figure 44:
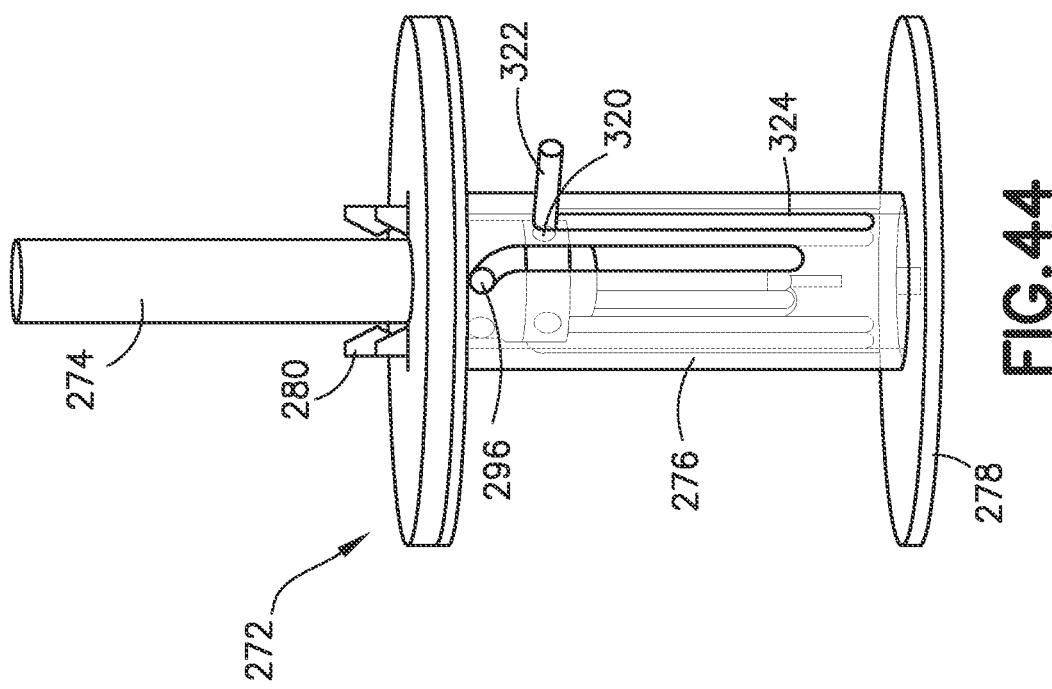
FIG. 44 is a perspective view of the needle hub of FIG. 41, showing a retracted position of a needle holder and a cannula holder with a portion of the needle hub transparent for clarity.
Figure 43:
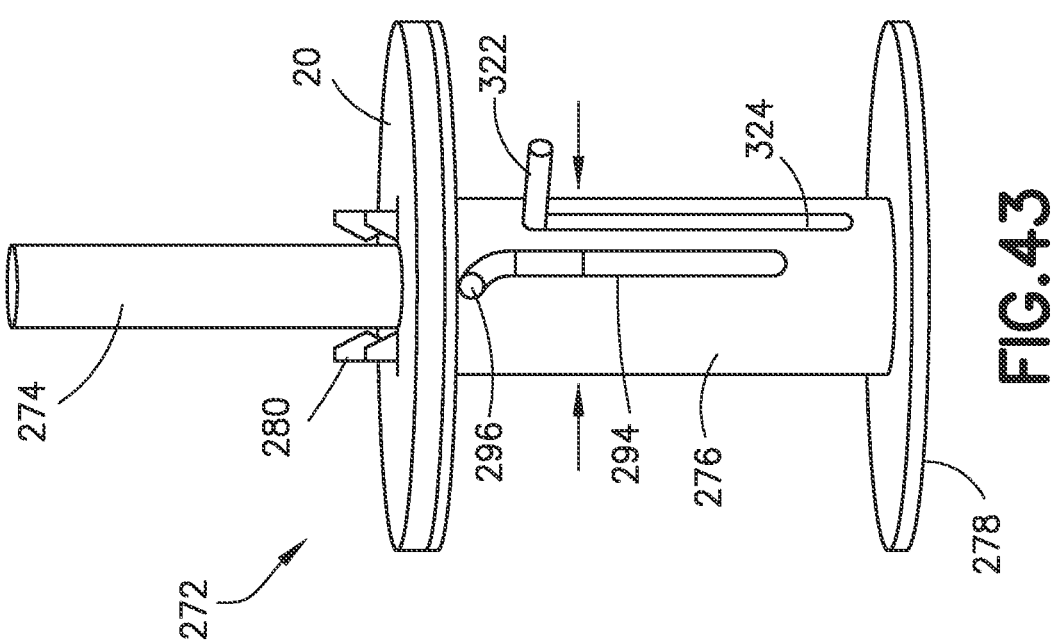
FIG. 43 is a perspective view of the needle hub of FIG. 41, showing a retracted position of a needle holder and a cannula holder.
Figure 45:
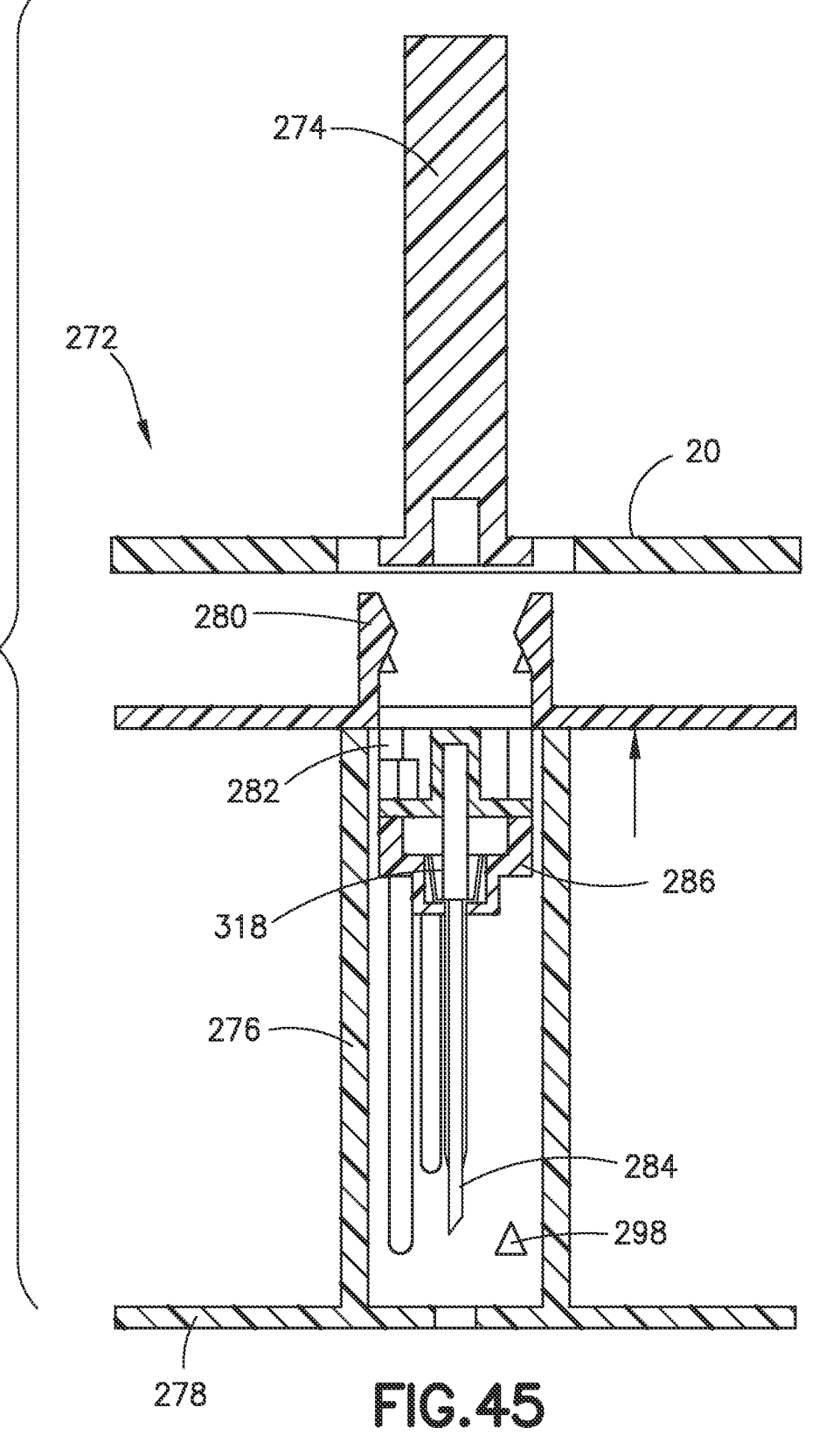
FIG. 45 is a cross-sectional view of the needle hub of FIG. 41, showing the needle hub being secured to a drug delivery device.
Figure 46:
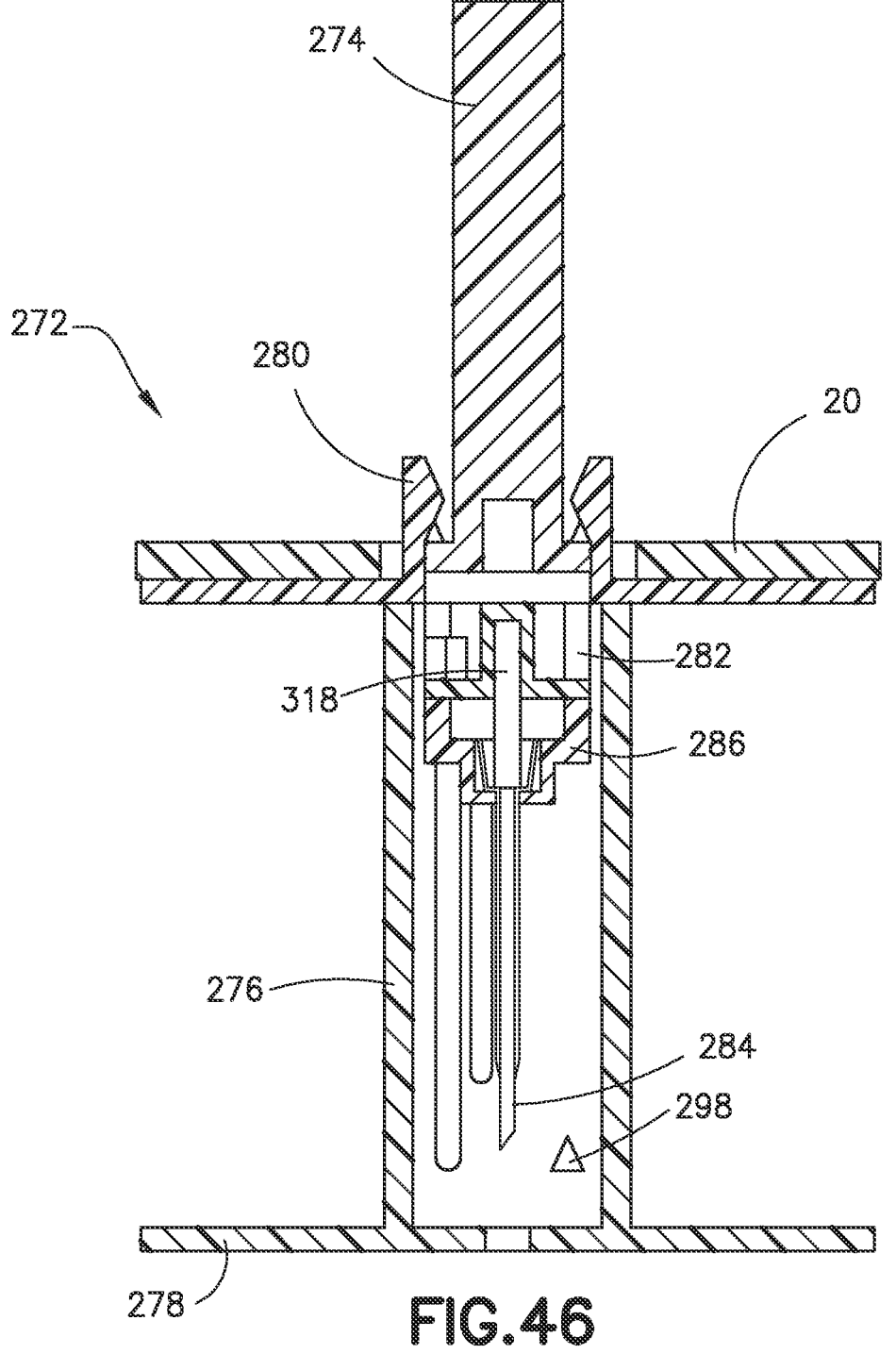
FIG. 46 is a cross-sectional view of the needle hub of FIG. 41, showing the needle hub secured to a drug delivery device.
Figure 47:
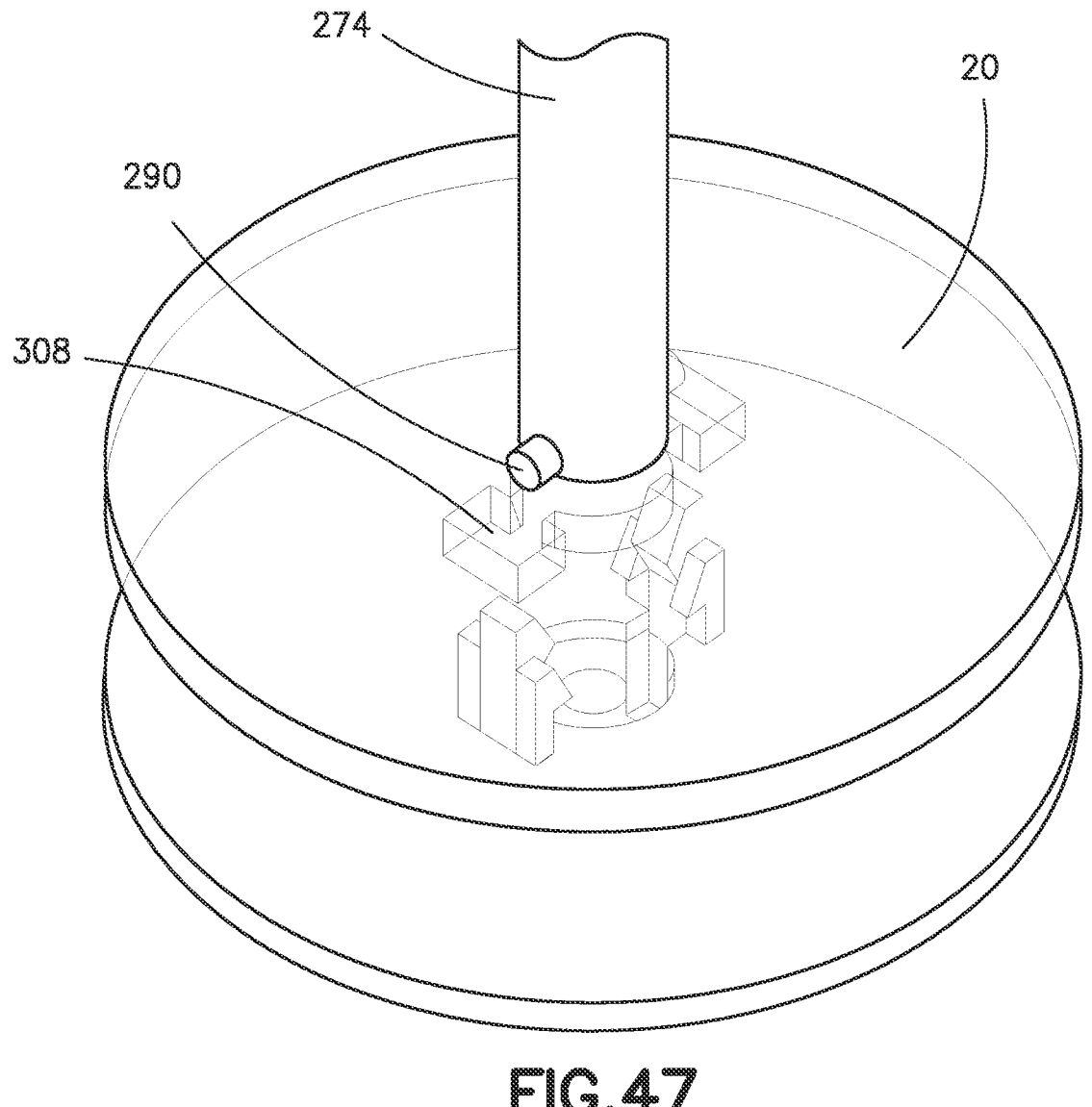
FIG. 47 is a partial perspective view of the needle hub of FIG. 41, showing an actuator interacting with the needle hub.

Referring to FIG. 40, the drug delivery devices in any of the aspects or embodiments discussed above may utilize a valve assembly 260 that engages a reservoir and/or container to facilitate the fluid connection between the reservoir and/or container and the fluid path to the needle and/or cannula. The valve assembly 260 may be similar to and operate in the same manner as the valve assembly shown and described in U.S. Patent Application Publication No. 2017/0354788.

Referring to FIGS. 41-55, a drug delivery device 270 and a needle hub 272, according to a further aspect or embodiment, is shown. The drug delivery device 270 may be similar to the drug delivery device 10 shown in FIGS. 1 and 2. In one aspect or embodiment, the drug delivery device 270 includes the housing 20, the fluid reservoir 12 received within the housing 20, and the drive mechanism 27 configured to dispense fluid from the fluid reservoir 12. The drug delivery device 270 further includes a needle hub actuator 274 attached to the housing 20. The needle hub 272 is at least partially received by the housing 20. The needle hub 272 includes a hub body 276 having a patient contact surface 278 and a housing connection 280 attaching the hub body 276 to the housing 20, a needle holder 282 with a needle 284 attached to the needle holder 282, and a cannula holder 286 with a cannula 288 attached to the cannula holder 286. The needle hub actuator 274 is configured to move the needle holder 282 and the cannula holder 286 from a retracted position where the needle 284 and the cannula 288 are positioned within the hub body 276 to an insertion position where the needle 284 and the cannula 288 are positioned within the hub body 276. The needle hub 272 is detachable from the housing 20.

Figure 48:
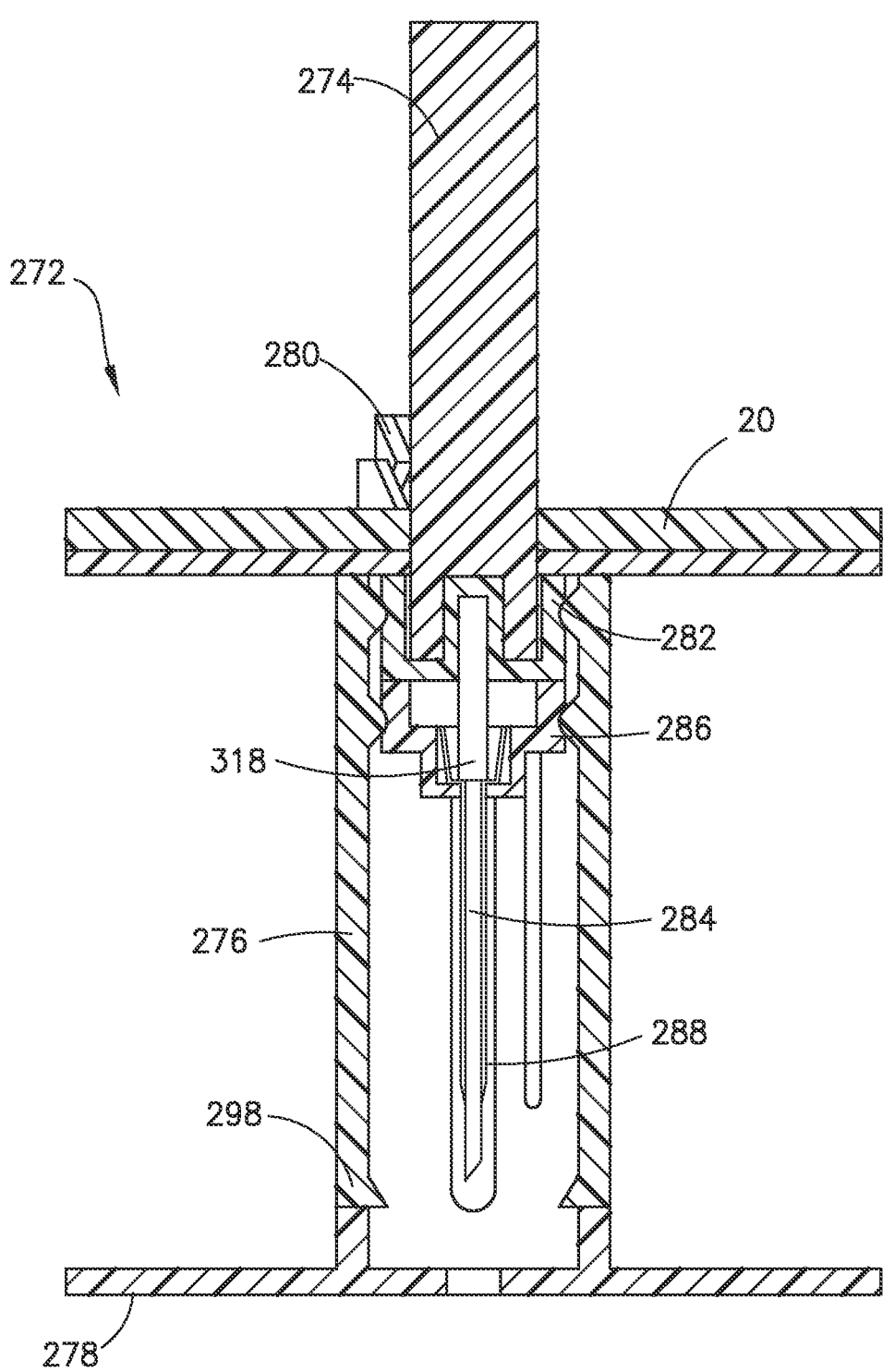
FIG. 48 is a cross-sectional view of the needle hub of FIG. 41, showing a needle holder engaged with an actuator.
Figure 49:
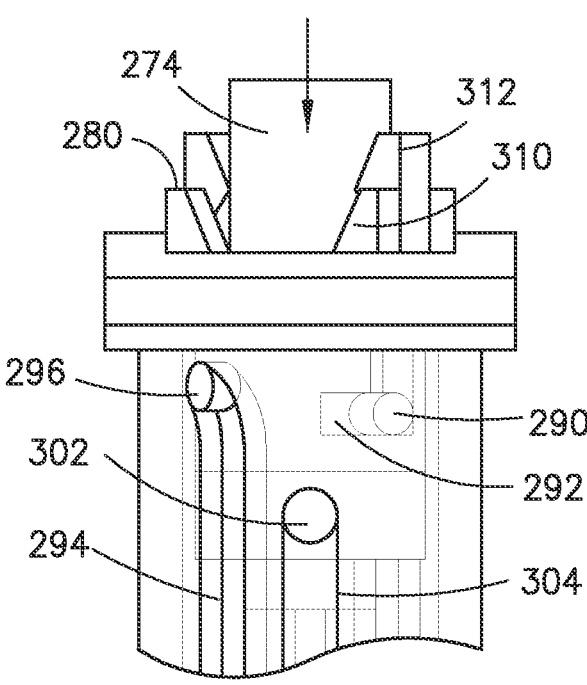
FIG. 49 is a partial perspective view of the needle hub of FIG. 41, showing a needle holder engaged with an actuator with a portion of the needle hub transparent for clarity.
Figure 50:
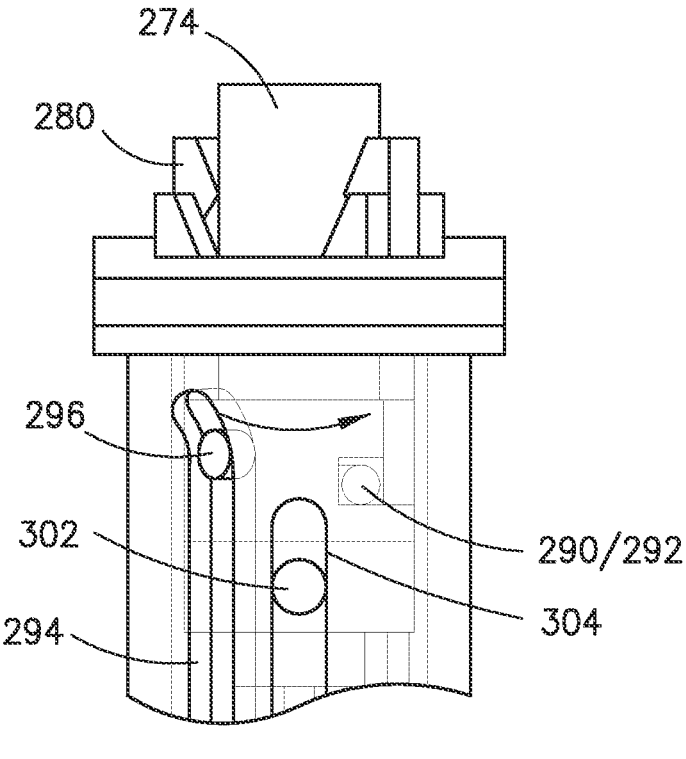
FIG. 50 is a partial perspective view of the needle hub of FIG. 41, showing a needle holder displaced by an actuator with a portion of the needle hub transparent for clarity.
Figure 51:
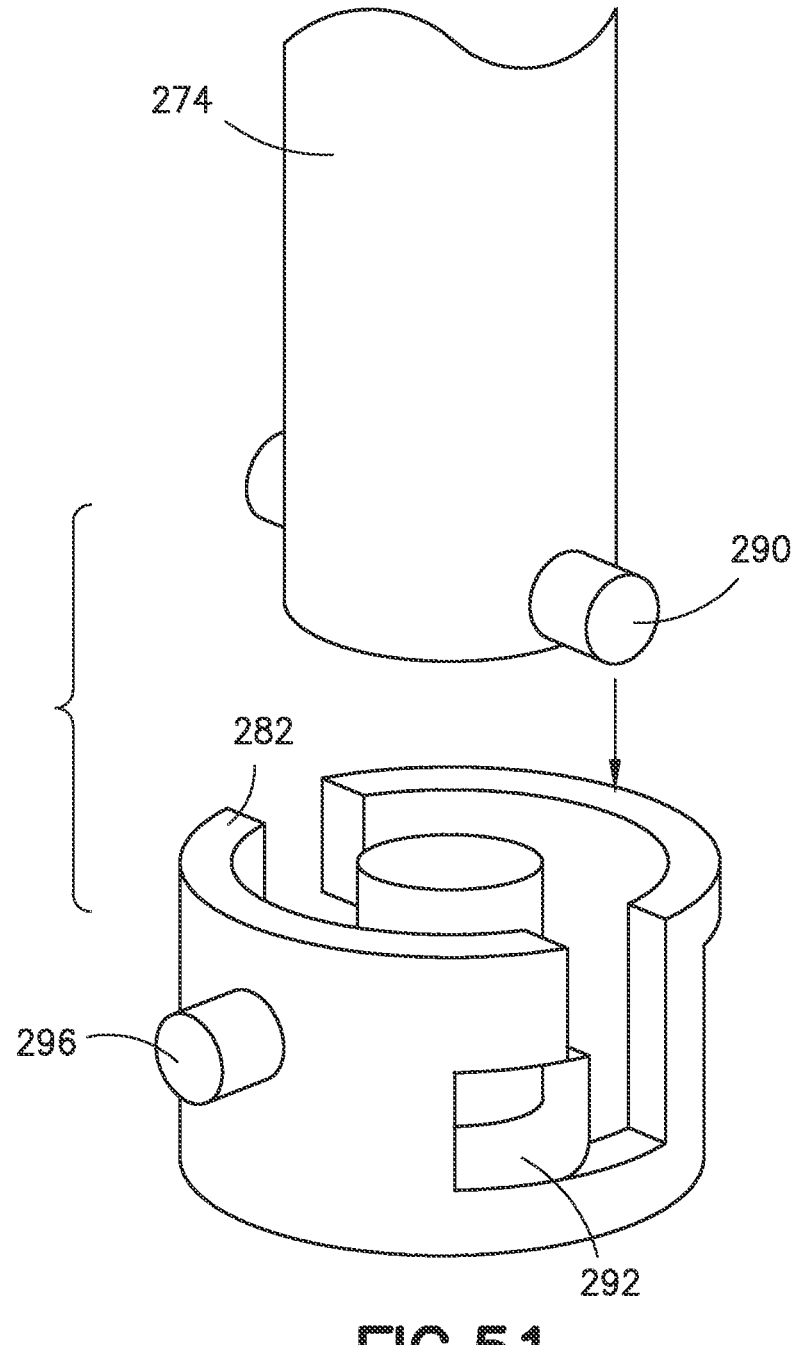
FIG. 51 is a partial perspective view of a needle holder and an actuator of the needle hub and the drug delivery device of FIG. 41.
Figure 52:
FIG. 52 is a cross-sectional view of the needle hub of FIG. 41, showing a needle holder and a cannula holder in an insertion position.
Figure 53:
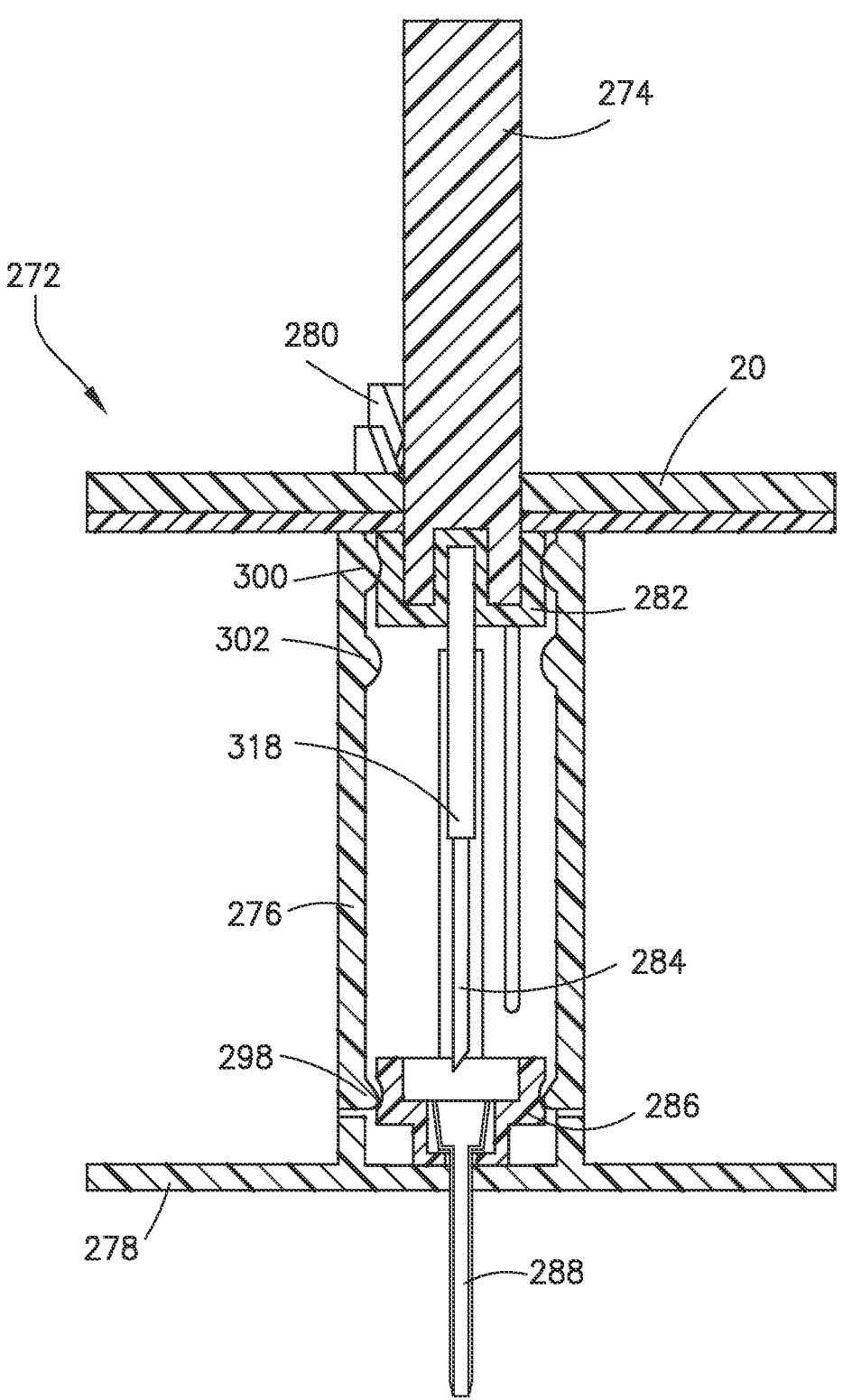
FIG. 53 is a cross-sectional view of the needle hub of FIG. 41, showing a needle holder in a retracted position and a cannula holder in an insertion position.
Figures 54, 55:
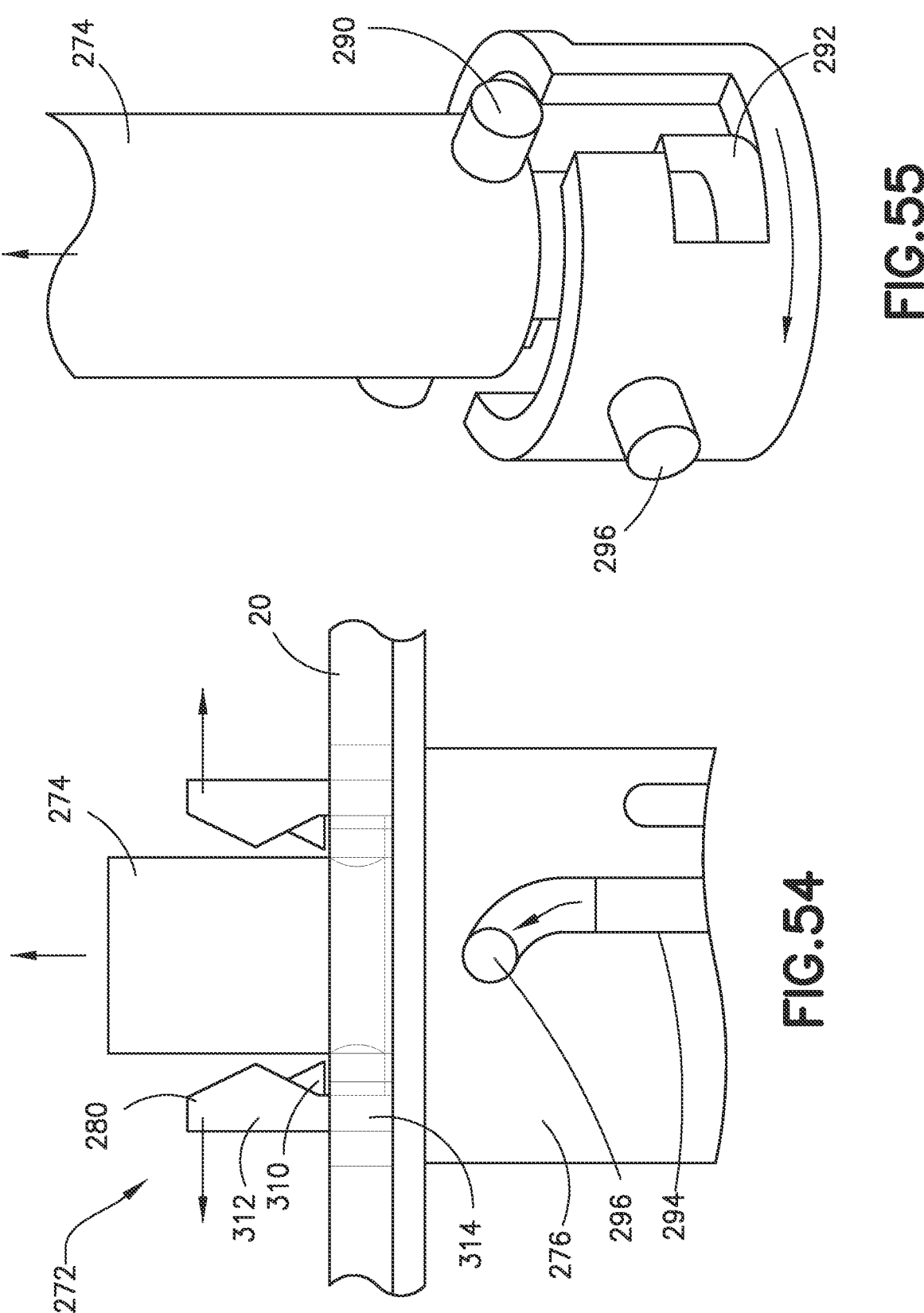
FIG. 54 is a partial front view of the needle hub of FIG. 41, showing an actuator releasing from the needle hub.
FIG. 55 is a partial perspective view of the needle hub of FIG. 41, showing an actuator releasing from a needle holder.

Referring to FIGS. 43-55, the needle hub actuator 274 includes a needle holder connector 290 and the needle holder 282 includes an actuator connector 292, with the needle holder connector 290 configured to be connected to the actuator connector 292. The hub body 276 defines a cam track 294 and the needle holder 282 includes a cam member 296 received within the cam track 294. Axial displacement of the needle holder 282 is configured to rotate the needle holder 282 to connect the needle holder connector 290 of the needle hub actuator 274 to the actuator connector 292 of the needle holder 282. As shown more clearly in FIGS. 49-51, the needle holder connector 290 of the needle hub actuator 274 and the actuator connector 292 of the needle holder 282 form a bayonet connector, although other suitable connection arrangements may be utilized. As shown in FIGS. 52 and 53, the hub body 276 includes a cannula lock 298 configured to secure the cannula holder 286 in the insertion position. In one aspect or embodiment, the cannula lock 298 is protrusion received by a corresponding recess of the cannula holder 286, although other suitable arrangements may be utilized. As shown in FIGS. 48, 52, and 53, the hub body 276 includes a needle protrusion 300 configured to engage the needle holder 282 when the needle holder 282 is in the retracted position, and the hub body 276 includes a cannula protrusion 302 configured to engage the cannula holder 286 when the cannula holder 286 is in the retracted position.

Referring again to FIGS. 41-55, the hub body 276 defines a cannula track 304 and the cannula holder 286 includes a track protrusion 306 received within the cannula track 304. The cannula track 304 is linear, which corresponds to the linear, non-rotating movement of the cannula holder 286 between the retracted position and the insertion position. As shown more clearly in FIG. 47, the housing connection 280 of the hub body 276 is received within an opening 308 defined by the housing 20. The housing connection 280 includes a retaining member 310 configured to engage the housing 20 to secure the hub body 276 to the housing 20. The housing connection 280 also includes a release member 312 configured to be engaged by the needle hub actuator 274 to release the hub body 276 from the housing 20. The retaining member 310 and the release member 312 are positioned on an extension 314, with the extension 314 configured to be biased radially outward. The patient contact surface 278 includes an adhesive pad 316 configured to secure the hub body 276 to a skin surface of a person. The cannula holder 286 includes a seal 318 engaged with the needle 284. The cannula holder 286 includes a port 320 in fluid communication with the cannula 288. The port 320 of the cannula holder 286 is in fluid communication with the fluid reservoir via tubing 322. The tubing 322 is received within a slot 324 defined by the hub body 276.

Referring again to FIGS. 43-55, at the time of assembly or post-assembly, the needle hub 272 is connected to the housing 20 of the drug delivery device 270 by inserting the retaining member 310 into the opening 308. The needle hub 272 is attached to a skin surface of a person by placing the needle hub 272, while attached to the drug delivery device 270, onto a skin surface and actuating the needle hub actuator 274. The needle hub actuator 274 is linearly or axially moveable relative to the drug delivery device 270. The needle hub actuator 274 may be driven by an electric motor, hydraulics, pneumatics, or other suitable arrangement. During initial movement of the needle hub actuator 274, the needle hub actuator 274 engages and axially moves the needle holder 282, which causes the needle holder 282 to rotate due to the cam member 296 moving through a curved portion of the cam track 294. The rotation of the needle holder 282 connects the needle hub actuator 274 to the needle holder 282 via the needle holder connector 290 and the actuator connector 292.

The needle hub actuator 274 continues to move axially to move the needle holder 282 and the cannula holder 286 to the insertion position (FIG. 52). The needle hub actuator 274 retracts with the needle holder 282 still secured to the needle hub actuator 274 thereby moving the needle holder 282 back to the retracted position. The cannula holder 286 remains in the insertion position due to the cannula lock 298 engaging the cannula holder 286. As the needle hub actuator 274 and the needle holder 282 reach their initial position, the needle holder 282 rotates again to the initial position of the needle holder 282, which releases the needle hub actuator 274 from the needle holder 282. As the needle hub actuator 274 is fully retracted, the needle hub actuator 274 engages the release member 312 of the housing connection 280 to deflect the housing connection 280 radially outward thereby releasing the needle hub 272 from the drug delivery device 270 to allow the drug delivery device 270 to be separated from the needle hub 272. The drug delivery device 270 can then infuse medication from the fluid reservoir 12, through the tubing 322, through the cannula 288, and into a patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A drug delivery device comprising:
   a housing;
   a fluid reservoir received within the housing;
   a drive assembly configured to dispense fluid from the fluid reservoir;
   a needle hub actuator attached to the housing; and
   a needle hub at least partially received by the housing, the needle hub comprising:
   a hub body comprising a patient contact surface and a housing connection attaching the hub body to the housing;
   a needle holder with a needle attached to the needle holder; and
   a cannula holder with a cannula attached to the cannula holder,
   wherein the needle hub actuator is moveable relative to the housing from a first position to a second position spaced from the first position, the second position of the needle hub actuator is closer to the patient contact surface of the hub body than the first position of the needle hub actuator, the needle hub actuator configured to move the needle holder and the cannula holder from a retracted position where the needle and the cannula are positioned within the hub body to an insertion position where distal ends of the needle and the cannula are positioned outside of the hub body, and wherein the needle hub is detachable from the housing, wherein the housing connection of the hub body is received within an opening defined by the housing, wherein the housing connection comprises a retaining member configured to engage the housing to secure the hub body to the housing, and wherein the housing connection comprises a release member, the release member of the housing connection engaging the needle hub actuator to release the hub body from the housing when the needle hub actuator moves from the second position to the first position.

2. The drug delivery device of claim 1, wherein the needle hub actuator comprises a needle holder connector and the needle holder comprises an actuator connector, the needle holder connector configured to be connected to the actuator connector.

3. The drug delivery device of claim 2, wherein the hub body defines a cam track and the needle holder comprises a cam member received within the cam track, and wherein axial displacement of the needle holder is configured to rotate the needle holder to connect the needle holder connector of the needle hub actuator to the actuator connector of the needle holder.

4. The drug delivery device of claim 3, wherein the needle holder connector of the needle hub actuator and the actuator connector of the needle holder form a bayonet connector.

5. The drug delivery device of claim 4, wherein the hub body comprises a cannula lock configured to secure the cannula holder in the insertion position.

6. The drug delivery device of claim 5, wherein the cannula lock comprises a protrusion configured to engage the cannula holder when the cannula holder is in the insertion position.

7. The drug delivery device of claim 3, wherein the hub body comprises a needle protrusion configured to engage the needle holder when the needle holder is in the retracted position, and wherein the hub body comprises a cannula protrusion configured to engage the cannula holder when the cannula holder is in the retracted position.

8. The drug delivery device of claim 3, wherein the hub body defines a cannula track and the cannula holder comprises a track protrusion received within the cannula track, and wherein the cannula track is linear.

9. The drug delivery device of claim 1, wherein the retaining member and the release member are positioned on an extension, the extension configured to be biased radially outward.

10. The drug delivery device of claim 1, wherein the patient contact surface comprises an adhesive pad configured to secure the hub body to a skin surface of a person.

11. The drug delivery device of claim 1, wherein the cannula holder comprises a seal engaged with the needle.

12. The drug delivery device of claim 11, wherein the cannula holder comprises a port in fluid communication with the cannula, and wherein the port of the cannula holder is in fluid communication with the fluid reservoir via tubing.

13. The drug delivery device of claim 12, wherein the tubing is received within a slot defined by the hub body.

14. The drug delivery device of claim 1, wherein the needle holder and the cannula holder are configured to be positioned within the housing when the needle hub actuator moves the needle holder and the cannula holder from the retracted position to the insertion position.

* * * * *